United States Patent
Briante et al.

(10) Patent No.: US 10,226,195 B2
(45) Date of Patent: Mar. 12, 2019

(54) ELECTRONIC SYSTEM TO CONTROL THE ACQUISITION OF AN ELECTROCARDIOGRAM

(71) Applicant: D-HEART S.R.L., Genoa (IT)

(72) Inventors: Nicolò Briante, Genoa (IT); Niccolò Maurizi, Florence (IT)

(73) Assignee: D-HEART S.R.L., Genoa (IT)

( * ) Notice: Subject to any disclaimer, the term of this patent is extended or adjusted under 35 U.S.C. 154(b) by 0 days.

(21) Appl. No.: 15/560,931

(22) PCT Filed: May 25, 2016

(86) PCT No.: PCT/IB2016/053063
§ 371 (c)(1),
(2) Date: Sep. 22, 2017

(87) PCT Pub. No.: WO2016/207745
PCT Pub. Date: Dec. 29, 2016

(65) Prior Publication Data
US 2018/0049659 A1  Feb. 22, 2018

(30) Foreign Application Priority Data
Jun. 22, 2015  (IT) .................. 102015000026025

(51) Int. Cl.
*A61B 5/00* (2006.01)
*A61B 5/04* (2006.01)
*A61B 5/0404* (2006.01)
*A61B 5/107* (2006.01)
*A61B 5/0408* (2006.01)
*A61B 5/0428* (2006.01)
*A61B 5/0472* (2006.01)

(52) U.S. Cl.
CPC ........ *A61B 5/04017* (2013.01); *A61B 5/0006* (2013.01); *A61B 5/0404* (2013.01); *A61B 5/04014* (2013.01); *A61B 5/684* (2013.01); *A61B 5/0428* (2013.01); *A61B 5/0472* (2013.01); *A61B 5/04085* (2013.01); *A61B 5/1079* (2013.01); *A61B 5/743* (2013.01); *A61B 2505/07* (2013.01)

(58) Field of Classification Search
CPC .................... A61B 5/04017; A61B 5/0006
USPC .......................................... 600/509
See application file for complete search history.

(56) References Cited

U.S. PATENT DOCUMENTS

2013/0215042 A1  8/2013  Messerschmidt et al.
2014/0333332 A1  11/2014  Matsumoto et al.

FOREIGN PATENT DOCUMENTS

GB  2489704  10/2012
JP  2014128455  7/2014

OTHER PUBLICATIONS

PCT/IB2016/053063, Oct. 31, 2016, Search Report and Written Opinion.

*Primary Examiner* — Nadia A Mahmood

(57) ABSTRACT

It is disclosed an electronic system to control the acquisition of an electrocardiogram. The system comprises a portable electronic device and a mobile electronic device. The mobile electronic device comprises an optical device for acquiring real-time images of a portion of a human body, a screen and a processing unit. The portable electronic device comprises a first, a second and a third electrode. The processing unit of the mobile electronic device comprises an electrodes placement guiding module for the first, second and third electrode. The screen is configured to display a real-time image representing said portion of the human body and further comprises a first positioning mark, a second positioning mark and a third positioning mark representing the positions wherein to apply the first, second and third electrode respectively.

12 Claims, 9 Drawing Sheets

ELECTRONIC SYSTEM TO CONTROL THE ACQUISITION OF AN ELECTROCARDIOGRAM

BACKGROUND

Technical Field

The present disclosure relates to an electronic system to control the acquisition of an electrocardiogram.

Description of the Related Art

The electrocardiogram (ECG) is very important in determining the presence of cardiovascular diseases.

For example, the electrocardiogram allows to determine the presence of acute myocardial infarct, localize the origin of an ischemia, diagnose the presence of tachyarrhythmia and monitor the therapy of patients with heart failure.

The electrocardiogram exploits the presence of transmembrane ionic currents flowing between the cell membrane and the adjacent cells. These currents are synchronised by the activation and by the sequences of cardiac recovery and create an electric field inside and around the heart.

Said electric field varies over time during a cardiac cycle and is transmitted to the structures adjacent to the heart, such as the lungs, blood, skeletal muscles and skin.

The currents reaching the skin are exploited for generating the track of an electrocardiogram and said currents are detected by means of electrodes appropriately positioned on the skin.

In particular, an electrocardiogram performed in a hospital environment uses ten electrodes and twelve unipolar, precordial unipolar and bipolar leads.

The tracks obtained from the recording of the signal generated by the leads represent the electrocardiogram.

The bipolar leads measure the potential difference between two electrodes, wherein one electrode is considered positive and one negative. In particular, the potential difference between the left arm (positive electrode) and the right arm (negative electrode), between the left leg (positive electrode) and the right arm (negative electrode) and between the left leg (positive electrode) and the left arm (negative electrode) is measured.

Unipolar leads on the other hand measure the electrical potential at the point wherein the electrodes are applied, which are typically positioned in the region of the precordium, about the front margin of the heart up to the tip thereof.

Moreover, it is possible to obtain three unipolar leads known as "boosted" which are obtained from the bipolar leads.

It is known that each cardiac cycle of a person in a stable physical state generate an electrocardiogram track that comprises, in order of time:
- a P wave representing the depolarisation of the heart atria;
- a QRS complex: it is a set of three waves representing the depolarisation of the heart ventricles;
- a T wave representing the repolarisation of the heart ventricles;
- a U wave (not always detectable) representing repolarisation of the papillary muscles.

The ten electrodes must be placed in specific anatomical positions, which is not always easy to recognise or identify, especially by non-medical personnel.

Some studies have demonstrated that four electrodes are sufficient to obtain an electrocardiogram that has a specificity and sensitivity that are statistically comparable with respect to an electrocardiogram obtained with ten electrodes (see in this matter Green et al., *American Journal of Cardiology*, 2004, 94:1529-1533).

One of the biggest challenges in modern Cardiology relates to the frequent dissociation between the presence of a symptom and the contemporary documentation of objective medical texts relating to it.

The use of traditional methods (ECG with 12 standard leads, continuous ECG in the 24 hours following the Holter method or recordings by external monitors for 7-30 days) for diagnosing cardiovascular conditions that are manifested occasionally has too often produced disappointing results; recent studies have also demonstrated how even continuous monitoring over 7 days has not succeeded in highlighting the cardiovascular condition causing the symptom the patient initially complains of.

A partial solution to these problematics has been offered by the introduction of subcutaneously implantable devices which operate a continuous recording of the heart's electrical activity. Notwithstanding everything, however, the implants are installed using an invasive procedure, have no utility in distinguishing transitory myocardial ischemia and nothing guarantees that the symptom complained of will manifest itself during the long but limited implant period.

Therefore there is a perceived need for immediately having a device which allows to acquire the electrocardiograph track at the exact moment wherein an acute pathological state occurs, so as to be able to correlate the electrocardiograph track to the particular pathological state.

U.S. Pat. No. 8,509,882 discloses a device transmitting, using Bluetooth technology, a signal representing an electrocardiogram to a smartphone, which displays said signal on the screen.

Patent application MX2013001001 discloses a monitoring device for an electrocardiogram with twelve leads, wherein the device comprises a Bluetooth communication module for transmitting the electrocardiogram to a mobile telephone, which displays the tracks of the electrocardiogram three at a time.

U.S. Pat. No. 8,005,531 discloses an apparatus for processing the electrocardiographic signals of a patient. The apparatus uses a plurality of algorithms, each specifically designed for analysing twelve leads, which can be measured or derived.

U.S. Pat. No. 6,282,440 discloses a method for determining whether the electrodes of an electrocardiogram are positioned correctly by means of the analysis of the signals generated by eight electrodes. In particular, a covariance matrix is calculated as a function of eight channels, the solution of the self-vectors of the covariance matrix is calculated, and the corners between the self-vectors and the original vectors are calculated. The values of the angles are compared with a set of reference angles and, as a function of this comparison, it is determined whether the electrodes are positioned correctly.

It is important to correctly position the electrodes for acquiring the heart's electrical activity, otherwise the acquired electocardiographic track will not be correct, i.e. it might generate false indications of cardiovascular diseases.

For example, the electrodes might not sufficiently adhere to the patient's skin or might be inverted.

In the case wherein the two electrodes are inverted, this can be the cause of a tracing exhibiting alterations of the atrial and ventricular depolarisation, thus providing a false indication of alterations of depolarisation.

Cardiopulmonary resuscitation is a first aid method of a patient in a state of cardiocirculatory arrest.

The survival of the patient in the condition of cardiocirculatory arrest depends on the rapid recognition of the condition of cardiocirculatory arrest, from correct positioning of the hands on the patient's chest and on the rate of the External Chest Compressions (Meaney P. et al., *AHA consensus statement: Cardiopulmonary Resuscitation Quality: Improvement Cardiac Resuscitation Outcomes Both Inside and Outside the hospital*, Circ. 2013, 128:417-435).

The Applicant has observed that the known devices have the following disadvantages:
- they do not provide a reliable guide to the placement of the electrodes;
- they do not allow a real-time verification of the correct placement of the electrodes on the patient's chest;
- they do not allow to immediately acquire a plurality of tracks of an electrocardiogram at the time wherein an alteration of the heart functioning is verified;
- they do not allow to immediately provide a correct guide to cardio-pulmonary resuscitation.

BRIEF SUMMARY

The present disclosure relates to an electronic system to control the acquisition of an electrocardiogram as defined in the enclosed claim 1 and by its preferred embodiments disclosed in the dependent claims from 2 to 8.

The Applicant has perceived that the electronic system according to the present disclosure has the following advantages:
- it provides a reliable guide to the placement of the electrodes, because it carries out a calibration of the placement according to the particular body form of the patient;
- it allows a real-time verification of the correct placement of the electrodes on the patient's chest;
- it immediately allows to acquire a track of an electrocardiogram at the time wherein an alteration of the heart functioning is verified;
- it immediately provides a correct guide to cardio-pulmonary resuscitation in a case of a cardiocirculatory arrest, ventricular tachycardia or ventricular fibrillation of a patient's heart.

One embodiment of the present disclosure is a method for controlling the acquisition of an electrocardiogram as defined in the enclosed claim 9, 10 and 11.

Another embodiment of the present disclosure is a computer readable medium having a program for controlling the placement of the electrodes for an electrocardiogram, as defined in the enclosed claim 12.

BRIEF DESCRIPTION OF THE SEVERAL VIEWS OF THE DRAWINGS

Additional features and advantages of the disclosure will become more apparent from the description which follows of a preferred embodiment and the variants thereof, provided by way of example in the appended drawings, wherein.

DETAILED DESCRIPTION

It should be observed that in the following description, identical or analogous blocks, components or modules are indicated in the figures with the same numerical references even where they are illustrated in different embodiments of the disclosure.

Figure 1:
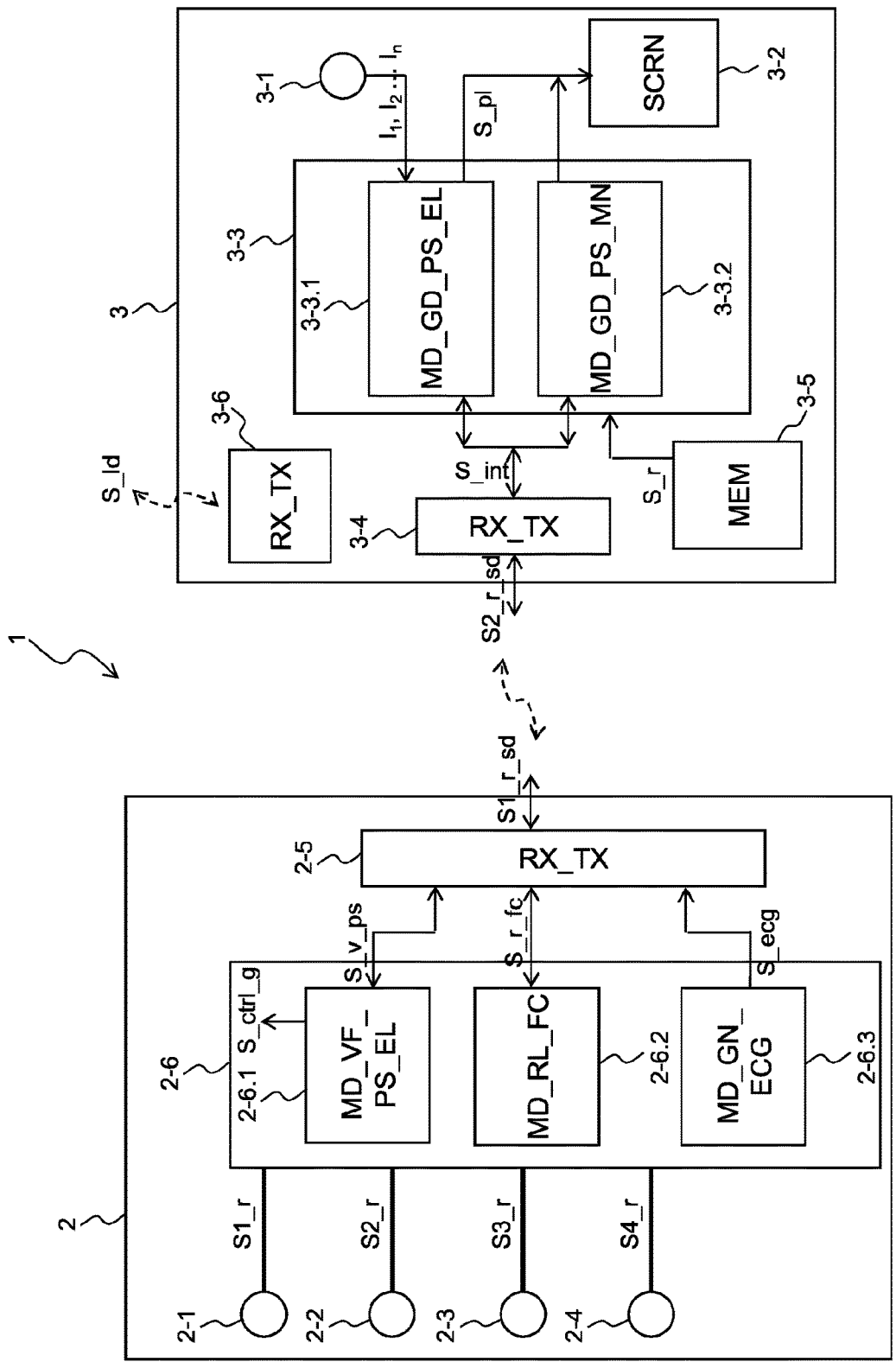
FIG. 1 shows a block diagram of the electronic system to control the acquisition of an electrocardiogram according to the disclosure.

With reference to FIG. 1, it shows an electronic system 1 to control the acquisition of an electrocardiogram according to the disclosure.

The electronic system 1 comprises a portable electronic device 2 and a mobile electronic device 3, which are connected each other by means of a short-range radio communication channel.

The term "short-range" means a distance of less than 10 meters.

The mobile electronic device 3 can be a smartphone (for example, an iPhone), a tablet (for example, an iPad) or a laptop.

The technology used to make the radio connection between the portable electronic device 2 and the mobile electronic device 3 is for example Bluetooth or WiFi (standard IEEE 802.11).

The mobile electronic device 3 comprises:
an optical device 3-1 for acquiring images;
a screen 3-2;
a transceiver 3-4 of short-range radio signals;
a processing unit 3-3;
a transceiver 3-6 of long-range signals.

The optical device 3-1 has the function of acquiring a plurality of real-time images $I_1, I_2 \ldots I_n$ representing a portion of a human body.

The optical device 3-1 is for example a camera or a videocamera.

The screen 3-2 is configured to display a real-time image representing the portion of the human body and to display textual indications, wherein said image further comprises a first positioning mark, a second positioning mark and a third positioning mark representing the positions wherein to apply the first, the second and the third electrodes respectively, as will be more fully described in the following.

The portion of the human body comprises for example the shoulders, the chest, the abdomen and the pelvis of a man, of a woman or of a child.

The transceiver 3-4 has the function of receiving/transmitting a short-range radio signal $S2\_r\_sd$ from/towards the portable electronic device 2.

The transceiver 3-6 of long-distance signals has the function of receiving/transmitting a long-range signal $S\_sd$ from/towards a medical centre or a central emergency unit for ambulance management. The long-range signal can be transmitted via a fixed communication network or can be of a radio-transmitted type via a network of radio-mobile communication.

The processing unit 3-3 has the function of controlling acquisition of an electrocardiogram of the heart of the human body, as will be explained more in detail in the following.

The processing unit 3-3 is electrically connected with the image acquisition optical device 3-1, with the screen 3-2, with the transceiver 3-4 and with the transceiver 3-6.

The processing unit 3-3 comprises:
- a first input terminal adapted to receive the plurality of images $I_1, I_2 \ldots I_n$ acquired from the optical device 3-1;
- an input/output terminal adapted to receive/transmit an internal signal S_int;
- a first output terminal adapted to generate a driving signal S_pl for driving the screen 3-2 with the purpose of viewing thereon appropriate images and/or textual indications.

In the case wherein the mobile electronic device 3 is a smartphone, the optical device 3-1 is the camera already incorporated into the smartphones actually available on the market; in particular, the camera is positioned on the front side of the smartphone (typically, above the screen of the smartphone) or on the rear side.

The portable electronic device 2 comprises:
- a first electrode 2-1;
- a second electrode 2-2;
- a third electrode 2-3;
- a transceiver 2-5 of short-range radio signals;
- a processing unit 2-6.

The portable electronic device 2 comprises a main body which is a closed casing (for example, made of a plastic material) which encloses the processing unit 2-6, wherein the electrodes 2-1, 2-2, 2-3 are connected to the main body by means of suitable electrical cables and possible interposed circuits.

Figure 3A:
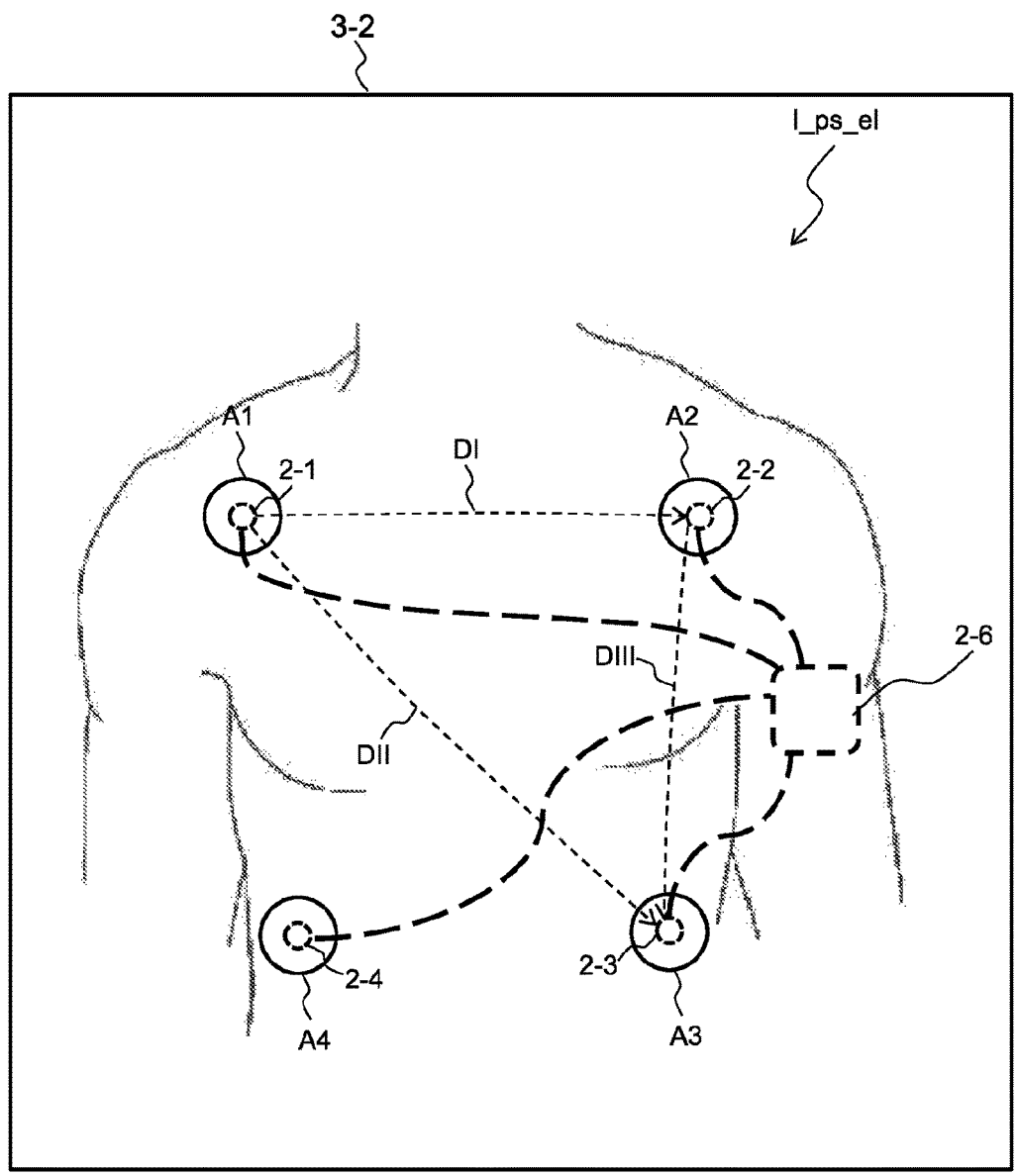
FIG. 3A schematically shows an image representing the position of the electrodes on the chest for carrying out an electrocardiogram.

The main body of the portable electronic device 2 has compact dimensions (for example, it has a square shape with a side of about 6 cm) and it is positioned in proximity of the human body on which the electrocardiogram is to be carried out; for example, the main body is fixed (by appropriate fixing means, for example a strap) to the arm of the human body, in particular on the biceps muscle as shown in FIG. 3A.

The first electrode 2-1, the second electrode 2-2 and the third electrode 2-3 are contacts (for example of resistive type) which detect a variation of analog voltage proportional to the current generated on the skin of the human body in the respective point wherein the electrodes 2-1, 2-2, 2-3 are positioned, following the heart beat of the considered human body.

The variation of current detected by each electrode 2-1, 2-2, 2-3 is converted into digital format by means of an analog-digital converter, as will be more fully explained in the following in relation to the description of FIG. 2.

In particular, the first electrode 2-1 is configured to generate a first detecting electrical signal S1_r representing the current generated on the skin by the activity of the heart of a human being analysed in the point wherein the first electrode 2-1 is positioned on the considered portion of the human body.

Likewise, the second electrode 2-2 is configured to generate a second detecting electrical signal S2_r representing the current generated on the skin by the activity of the heart of a human being analysed in the point wherein the second electrode 2-2 is positioned on the considered portion of the human body.

Lastly the third electrode 2-3 is configured to generate a third detecting electrical signal S3_r representing the current generated on the skin by the activity of the heart of a human being analysed in the point wherein the third electrode 2-3 is positioned on the considered portion of the human body.

Advantageously, the portable electronic device 2 further comprises a fourth electrode 2-4 representing a reference ground voltage and has the purpose of discharging the current detected on the skin and minimising the difference in impedance between the different electrodes 2-1, 2-2, 2-3 and the skin.

The fourth electrode 2-4 is connected to the main body (in particular, to the processing unit 2-6) by means of a respective electric cable and possible interposed circuits.

The transceiver 2-5 has the function of receiving/transmitting a short-range radio signal S1_r_sd from/towards the mobile electronic device 3.

The processing unit 2-6 has the function of controlling acquisition of an electrocardiogram of the heart of the human body, as will be explained more in detail in the following.

The processing unit 2-6 is electrically connected to the first 2-1, to the second 2-2, to the third 2-3, to the fourth 2-4 electrode and with the transceiver 2-5.

The processing unit 2-6 comprises:
- a first output terminal adapted to generate a positioning verification signal S_v_ps indicating the correct placement of the first electrode 2-1, of the second electrode 2-2 and of the third electrode 2-3;
- a second output terminal adapted to generate a heart rate detection signal S_r_fc indicating a presence of a cardiocirculatory arrest or a ventricular fibrillation or a ventricular tachycardia of the heart of the human body analysed;
- a third output terminal adapted to generate an electrocardiogram signal S_ecg carrying the tracks representing the electrocardiogram of the heart of the human body analysed;
- a first, second, third and fourth input terminal adapted to receive the first, second, third and fourth detecting electrical signals S1_r, S2_r, S3_r and S4_r respectively.

In one embodiment the processing unit 2-6 is structured to further generate a gain control signal S_ctrl_g for regulating the value of the gain of an amplification circuit 2-8, as will be explained in greater detail in the following.

In greater detail, the processing unit 3-3 of the mobile electronic device 3 comprises:
- an electrodes placement guiding module 3-3.1 for the first, second and third electrodes 2-1, 2-2, 2-3, (and possibly the fourth electrode 2-4) which will be indicated in the following as "electrodes placement guiding module 3-3.1";
- a hand placement guiding module 3-3.2 for positioning of the hands, indicated in the following as "hand placement guiding module".

In greater detail, the processing unit 2-6 of the portable electronic device 2 comprises:
- an electrodes placement verification module 2-6.1 for the first, second and third electrodes 2-1, 2-2, 2-3 (and possibly a fourth electrode 2-4) which will be indicated in the following as "electrodes placement verification module 2-6.1";
- a heart rate detecting module 2-6.2;
- an electrocardiogram generating module 2-6.3.

The electrodes placement guiding module 3-3.1 has the function of guiding any person to position the electrodes 2-1, 2-2, 2-3 on a portion of the human body (for example, the chest) with the purpose of acquiring an electrocardiogram of the heart of the human body.

Note that the person acquiring the electrocardiogram is not necessarily a doctor or a member of medical personnel, but can also be, for example, the patient himself.

In particular, the electrodes placement guiding module 3-3.1 is configured to:
- receive, from the optical device 3-1 for acquiring images, a plurality of real-time images $I_1, I_2 \ldots I_n$ representing a determined portion of the analysed human body;
- identify a feature of the portion of the human body within at least part of said plurality of images $I_1, I_2 \ldots I_n$;
- calculate, as a function of the identified feature, the positions wherein to apply the first electrode 2-1, the second electrode 2-2 and the third electrode 2-3 on the considered portion of the analysed human body;
- generate a driving signal S_pl carrying information indicating the calculated positions wherein to apply the first electrode 2-1, the second electrode 2-2 and the third electrode 2-3.

The term "identifying a feature of the portion of the human body" is taken to mean the recognition of a feature of the human body using a suitable images processing algorithm.

Said recognition algorithms analyse, for example, the shape, the dimensions, the relative position of the searched features and compare them with respect to a plurality of predefined templates with the purpose of finding which of them is the closest one.

The recognition algorithms can be of a geometric type or a statistical type.

Some examples of recognition algorithms are the following:
- methods based on sub-spaces;
- neural networks;
- deformable models;
- "Support Vector Machines";
- "Hidden Markov Models".

In one embodiment the identified feature of the portion of the human body is a human shoulder.

Therefore the screen 3-2 of the mobile electronic device 3 is configured to receive the driving signal S_pl and to display an electrodes positioning real-time image I_ps_el representing the considered portion of the human body analysed, as shown in FIG. 3A, wherein said electrodes positioning image I_ps_el further comprises:
- a first positioning mark representing a position wherein to apply the first electrode 2-1;
- a second positioning mark representing a position wherein to apply the second electrode 2-2;
- a third positioning mark representing a position wherein to apply the third electrode 2-3;
- a fourth positioning mark representing a position wherein to apply the fourth electrode 2-4.

In one embodiment the first, second, third and fourth positioning marks are constituted by respective positioning areas A1, A2, A3 and A4. In this case the electrodes positioning image I_ps_el comprises the first positioning area A1 inside which the first electrode 2-1 must be positioned, the second positioning area A2 inside which the second electrode 2-2 must be positioned, the third positioning area A3 inside which the third electrode 2-3 must be positioned and, in particular, the fourth positioning A4 area inside which the fourth electrode 2-4 must be positioned (see FIG. 3A again): this provides a reliable guide to the placement of the electrodes 2-1, 2-2, 2-3 (and possibly 2-4), as the application positions of the electrodes 2-1, 2-2, 2-3 are shown graphically, superposed on the image of the considered portion of the analysed human body.

Note that in FIG. 3A a continuous line shows the electrodes positioning image I_ps_el effectively displayed on the screen 3-2 of the mobile electronic device 3 and a broken line shows the electrodes 2-1, 2-2, 2-3, 2-4 and the processing unit 2-6 superposed on the electrodes positioning image I_ps_el.

According to a first variant of the disclosure, the portion of the analysed human body comprises the shoulders, the chest, the abdomen and the pelvis (refer again to the image shown in FIG. 3A): in this case the feature of the portion of the human body (identified by means of a suitable recognition algorithm that processes images) is for example one of the two shoulders.

According to said first variant, the first positioning mark (for example, an area A1) is positioned on the chest of the human body analysed in proximity of the left shoulder, the second positioning mark (in the example the area A2) is positioned on the chest of the human body analysed in proximity of the right shoulder, the third positioning mark (in the example the area A3) is positioned on the abdomen of the human body analysed in proximity of the left leg and, in particular, the fourth positioning mark (in the example the area A4) is positioned on the abdomen of the human body analysed in proximity of the right leg (refer again to FIG. 3A).

Therefore the first electrode 2-1 is positioned on the chest in proximity of the left shoulder, the second electrode 2-2 is positioned on the chest in proximity of the right shoulder and the third electrode 2-3 is positioned on the abdomen in proximity of the left leg.

Figure 3B:
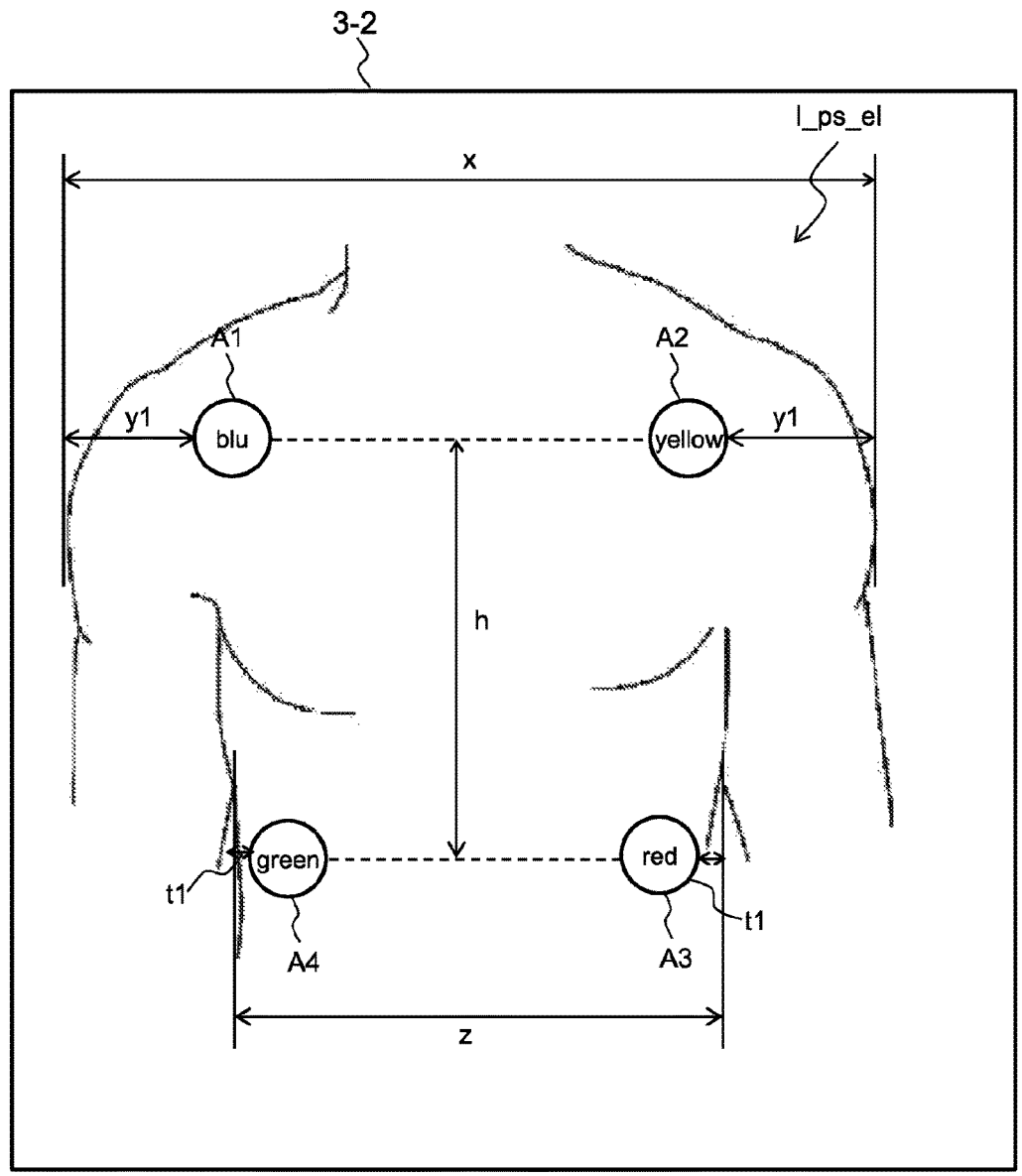
FIG. 3B shows in more detail the position of the electrodes of the illustration of FIG. 3A.

With reference to FIG. 3B, according to said first variant the electrodes placement guiding module 3-3.1 is configured to:
- receive the plurality of real-time images $I_1, I_2 \ldots I_n$ representing the shoulders, chest, abdomen and pelvis of the human body;
- identify the position of the shoulders within at least part of said plurality of images $I_1, I_2, \ldots I_n$;
- calculate the width x of the shoulders as a function of at least part of said plurality of images $I_1, I_2, \ldots I_n$;
- calculate, as a function of the width x of the shoulders and a first parameter k, a first distance y1 between the first positioning area A1 and the extremity of the right shoulder and between the second positioning area A2 and the extremity of the left shoulder;
- calculate the width z of the pelvis;
- calculate, as a function of the width z of the pelvis and a second parameter r, a second distance t1 between the third positioning area A3 and the extremity of the left pelvis;
- calculate a third distance h between the third positioning area A3 and the first positioning area A1 equal to a value x/2 comprised in an interval centred around half the width x of the shoulders (i.e. h=x/2±Δ, wherein Δ is a small value selected appropriately);
- generate the driving signal carrying information indicating the first distance y1, the second distance t1 and the third distance h.

Note that in the first variant the width of the chest of the analysed human body is measured by means of a suitable processing of the images $I_1, I_2 \ldots I_n$ acquired by the optical device 3-1: this has the advantage of performing a calibration of the position wherein to apply the electrodes 2-1, 2-2, 2-3 on the patient's chest as a function of the particular dimensions of the analysed patient's chest, thus reducing the probability of committing errors in the placement of the electrodes 2-1, 2-2, 2-3 on the chest.

With the term "first distance y1" (referring to the first positioning area A1) is meant the distance from the extremity of the left shoulder of the point belonging to the perimeter of the first positioning area A1 which is nearest the left shoulder and the distance from the extremity of the right shoulder of the point belonging to the perimeter of the second positioning area A2 which is nearest the right shoulder.

Likewise, with the term "second distance t1" (referring to the third positioning area A3) is meant the distance from the extremity of the left pelvis of the point belonging to the perimeter of the third positioning area A3 which is nearest the left pelvis.

Lastly, with the term "third distance h" (referring to the distance between the third positioning area A3 and the first positioning area A1) is meant the distance between a first straight line which joins a reference point inside the first positioning area A1 with a reference point inside the second positioning area A2 (i.e. the first straight line is the one joining the two shoulders) and a second straight line which joins a reference point inside the third positioning area A3 with a reference point inside the fourth positioning area (A4) (i.e. the second straight line is the one joining the two extremity of the pelvis), wherein the direction of the third distance h is perpendicular to the first straight line and the second straight line.

In the first variant of the disclosure, the screen 3-2 of the mobile electronic device is configured to receive the driving signal S_pl and to display the electrodes positioning real-time image I_ps_el representing at least the chest of the human body, wherein said image further comprises:
  the first positioning area having a position identified by the first distance y1;
  the second positioning area A2 having a position identified by the first distance y1;
  the third positioning area A3 having a position identified by the second distance t1 and by the third distance h.

In other words, the value of the first parameter k=x/y1 and the value of the second parameter r=z/t1 are fixed, then the width x of the shoulders is calculated by means of a suitable processing of at least a part of the plurality of images $I_1$, $I_2$, ... $I_n$ acquired by the optical device 3-1, then it is calculated the first distance y1 from the left/right shoulder at which to position the first/second positioning area A1/A2 by means of the calculation y1=k/x, then the width z of the pelvis is calculated, then the second distance t1 is calculated from the extremity of the left pelvis by means of the calculation t1=z/r, then it is calculated the third distance h between the first positioning area A1 and the third positioning area A3 by means of the calculation h=x/2, lastly the third positioning area A3 is positioned at the second distance t1 from the extremity of the left pelvis and at the third distance h=x/2 of the first positioning area A1 (see FIG. 3B).

In the case wherein the fourth electrode 2-4 is present, the position of the fourth positioning area A4 is identified (inside which to position the fourth electrode 2-4) in a similar way as the third positioning area A3. In particular, the fourth positioning area A4 is positioned at the second distance t1 from the extremity of the right pelvis and at the third distance h=x/2±Δ between the fourth positioning area A4 and the second positioning area A2.

In one embodiment the shape of the first positioning mark, of the second positioning mark, of the third positioning mark (and possibly the fourth positioning mark) is an "X".

Alternatively, in case wherein the positioning marks are constituted by an area, the shape of the first positioning area A1, of the second positioning area A2, of the third positioning area A3 (and possibly of the fourth positioning area A4) is a circle, thus obtaining four circles A1, A2, A3, A4. In this case the reference points (used for defining the third distance h) are the centres of the respective circles.

The four circles A1, A2, A3, A4 are positioned so as not to be superposed and so that the first circle A1 is aligned to the second circle A2, while the third circle A3 is aligned to the fourth circle A4.

Alternatively, the shape of the first positioning area A1, of the second positioning area A2, of the third positioning area A3 and of the fourth positioning area A4 is a rectangle, thus obtaining four rectangles A1, A2, A3, A4. In this case the reference points are the crossing points of the diagonals of the respective rectangles. The four circles A1, A2, A3, A4 are positioned so as not to be superposed and so that the first rectangle A1 is aligned to the second rectangle A2, while the third rectangle A3 is aligned to the fourth rectangle A4.

Advantageously, the first, second, third and fourth electrode 2-1, 2-2, 2-3, 2-4 comprise respective identifying means. In particular:
  the first electrode 2-1 comprises first identifying means;
  the second electrode 2-2 comprises second identifying means;
  the third electrode 2-3 comprises third identifying means;
  the fourth electrode 2-4 comprises fourth identifying means;

In this case the memory 3-5 is configured to store information associating a first graphic identifier to the first identifying means, a second graphic identifier to the second identifying means and a third graphic identifier to the third identifying means (and possibly a fourth graphic identifier associated to the fourth identifying means).

Further, the electrodes placement guiding module 3-3.1 is further configured to generate the driving signal S_pl carrying further information indicating the first, second and third graphic identifiers (and possibly the fourth graphic identifier).

Moreover, the screen 3-3 of the mobile electronic device 3 is configured to receive the driving signal and to display the image of the human body comprising the first graphic identifier inside the first positioning area A1, the second graphic identifier inside the second positioning area A2 and the third graphic identifier inside the third positioning area A3 (and possibly a fourth graphic identifier inside the fourth positioning area A4).

In particular, the first electrode 2-1 comprises first identifying means which are a blue-coloured surface, the second electrode 2-2 comprises second identifying means which are a yellow-coloured surface, the third electrode 2-3 comprises third identifying means which are a red-coloured surface and the fourth electrode 2-4 comprises fourth identifying means which are a green-coloured surface; in this case the screen 3-3 of the mobile electronic device 3 is configured to display the first positioning area A1 which is coloured blue, the second positioning area A2 having a yellow colour, the third positioning area A3 having a red colour and the fourth positioning area A4 having a green colour.

The electrodes placement verification module 2-6.1 of the processing unit 2-6 of the portable electronic device 2 has the function of verifying whether the electrodes 2-1, 2-2, 2-3 have not been positioned correctly on the patient's chest, for example because they have been inverted or are not correctly adhering to the patient's skin: this is obtained by exploiting Einthoven's law which defines that the arrangement of the electrodes of the leads DI, DII, DIII forms a triangle and that at each instant of the heart cycle the algebraic sum of the leads DI, DII, DIII is zero.

In particular, the electrodes placement verification module 2-6.1 is configured to:

receive the first detecting electrical signal S1-r generated by the first electrode 2-1, the second detecting electrical signal S2_r generated by the second electrode 2-2 and the third detecting electrical signal S3_r generated by the third electrode 2-3.

calculate a first lead DI equal to a first potential difference between the second detecting electrical signal S2_r and the first detecting electrical signal S1_r (see DI in FIG. 3A);

calculate a second lead DII equal to a second potential difference between the third detecting electrical signal S3_r and the first detecting electrical signal S1_r (see DII in FIG. 3A);

calculate a third lead DIII equal to a third potential difference between the third detecting electrical signal S3_r and the second detecting electrical signal S2_r (see DIII in FIG. 3A);

calculate a difference equal $\Delta_{II-I}$ to the difference between the second and the first potential difference;

verify whether the absolute value of the difference between the calculated difference $\Delta_{II-I}$ and the third potential difference is lower than or equal to a tolerance value $\varepsilon$;

in case of a positive verification, generate a positioning verification signal S_v_ps indicating the correct placement of the first, second and third electrodes;

in case of a negative verification, generate a positioning verification signal S_v_ps indicating the incorrect placement of at least one electrode among the first, second and third electrodes 2-1, 2-2, 2-3.

The tolerance value $\varepsilon$ is selected so as to be sufficiently small (in the order of millivolts).

Figure 3C:
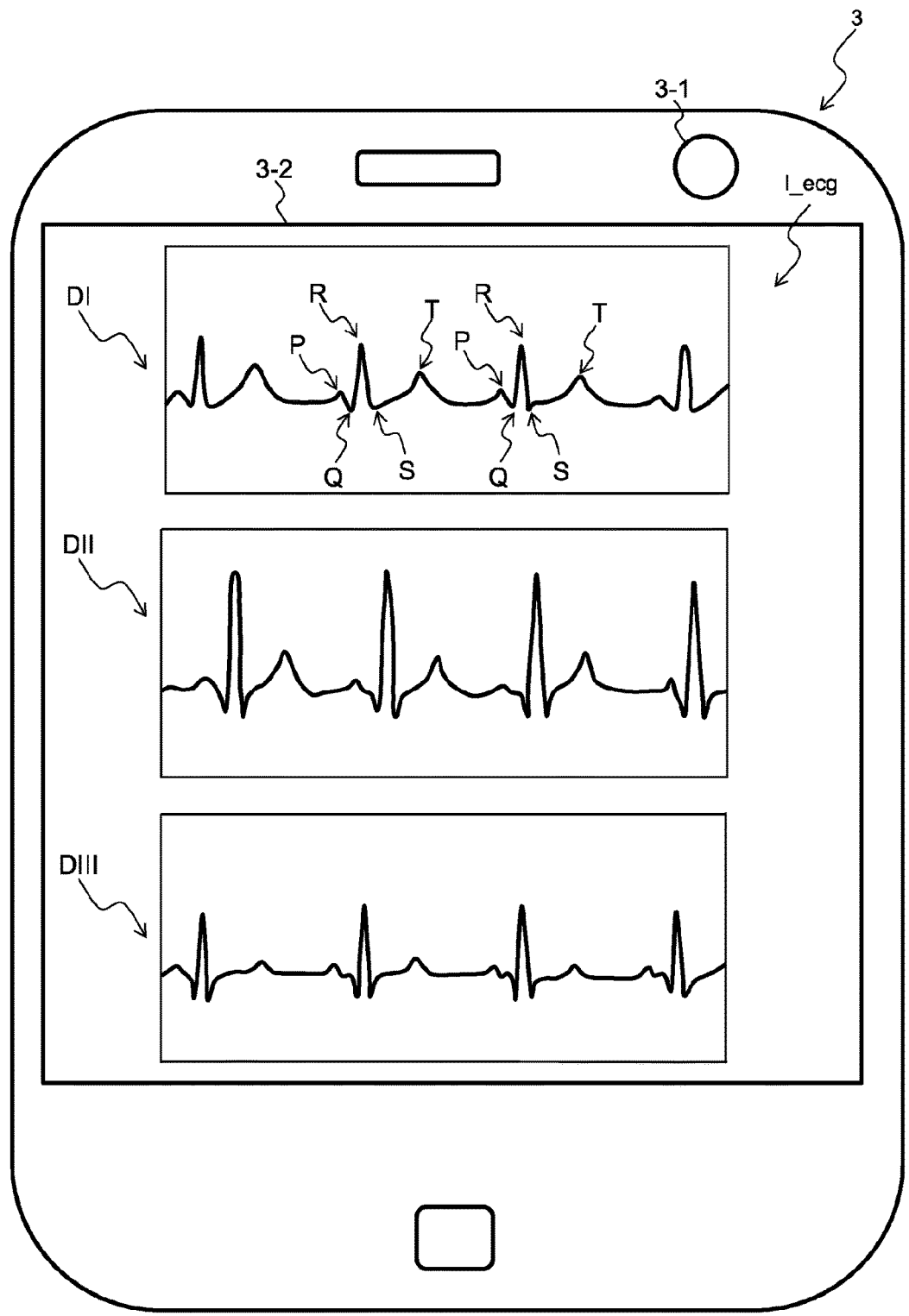
FIG. 3C shows the trend of the tracks of the electrocardiogram displayed on the screen of the mobile electronic device according to the disclosure.

FIG. 3C shows a possible trend of the tracks generated by the leads DI, DII, DIII of the heart of a person who is in a stable physical state, i.e. does not present symptoms of a cardiovascular condition.

In lead DI it is possible to observe the presence of P waves, of QRS complex and T wave (for simplicity these have not been shown in leads DII and DIII).

The transceiver 2-5 of the portable electronic device 2 is configured to receive the positioning verification signal and to generate therefrom a short-range radio signal S1_s_rd carrying information indicating the correct placement of the first, second and third electrodes 2-1, 2-2, 2-3 or indicating the incorrect placement of at least one electrode out of the first, second and third electrodes 2-1, 2-2, 2-3.

The transceiver 3-4 of the mobile electronic device 3 is configured to receive a short-range radio signal S2_s_rd carrying said information indicating the correct or incorrect placement and to generate therefrom an internal signal S_int carrying said information indicating the correct or incorrect placement.

The screen 3-2 of the mobile electronic device 3 is configured to receive the internal signal S_int and to display a graphic or textual indication representing the correct placement of the first, second and third electrodes 2-1, 2-2, 2-3 or indicating the incorrect placement of at least one electrode out of the first, second and third electrodes 2-1, 2-2, 2-3. For example, the screen 3-2 first displays a text or graphic message with a flashing intensity in case wherein at least one electrode is not correctly positioned, then it displays the real-time image of the portion of the human body (comprising for example the chest) so as to allow a new placement of the electrodes 2-1, 2-2, 2-3.

The heart rate detecting module 2-6.2 has the function of detecting the presence of a cardiocirculatory arrest or a ventricular fibrillation or a ventricular tachycardia of the heart of the analysed human body.

In particular, the heart rate detecting module 2-6.2 is configured to;

receive the first, second and third detecting electrical signals S1_r, S2_r, S3_r and to measure, as a function thereof, a distance (measured in milliseconds) between two successive R waves and the respective amplitude value (in millivolts) in a defined time interval;

if the amplitude value of the R waves is lower than a first amplitude threshold value close to zero, generate a heart rate detection signal S_r_fc having a first value indicating the presence of a cardiocirculatory arrest of the heart of the human body;

if the amplitude value of the R waves is comprised between the first amplitude threshold value and a second amplitude threshold value (greater than the first amplitude threshold value) and moreover if the value of said distance is lower than a first distance threshold value, generate the heart rate detection signal S_r_fc having a second value indicating the presence of ventricular fibrillation of the heart of the human body;

if the value of said distance is comprised between the first distance threshold value and a second distance threshold value (greater than the first distance threshold value), generate the heart rate detection signal S_r_fc having a third value indicating the presence of ventricular tachycardia of the heart of the human body.

The heart rate detecting module 2-6.2 can operate in a similar way taking into consideration the QRS complex instead of the R wave, thus the previous considerations relating to cardiocirculatory arrest, ventricular fibrillation and ventricular tachycardia detecting modes are applicable in a similar way using the QRS complex.

The transceiver 2-5 of the portable electronic device 2 is configured to receive the heart rate detection signal S_r_fc and to generate therefrom the short-range radio signal S1_s_rd carrying information indicating the presence of a cardiocirculatory arrest, ventricular fibrillation or ventricular tachycardia.

The transceiver 3-4 of the mobile electronic device 3 is configured to receive a short-range radio signal S2_s_rd carrying said information indicating the presence of a cardiocirculatory arrest, ventricular fibrillation or ventricular tachycardia and to generate therefrom an internal signal S_int carrying said information indicating the presence of a cardiocirculatory arrest, ventricular fibrillation or ventricular tachycardia, The memory 3-5 stores a video representing a guided procedure for cardiopulmonary resuscitation, said video containing a sequence of images and sounds representing the position of the hands to be applied on the chest of the human body and the number of pressures exerted by the hands on the chest.

The hand placement guiding module 3-3.2 has the function of guiding any person to correctly position his/her hands on the patient's chest with the purpose of carrying out a cardio-pulmonary resuscitation procedure.

In particular, the hand placement guiding module 3-3.2 is configured to:

receive the information indicating the presence of a cardiocirculatory arrest, ventricular fibrillation or ventricular tachycardia;

receive, from the images acquisition optical device 3-1 a plurality of real-time images $I_1, I_2 \ldots I_n$ representing a considered portion of the analysed human body;

identify said feature of the portion of the human body within at least part of said plurality of images;

calculating, as a function of the identified feature, the position wherein to apply the first and the second electrode on the chest of the human body;

calculate, as a function of the calculated position of the first and second electrodes, the position wherein to apply the hands on the sternum of the human body in order to perform a sequence of hand movements for a cardiopulmonary resuscitation of the heart of the human body;

generate the driving signal S_pl indicating the presence of a cardiocirculatory arrest, ventricular fibrillation or ventricular tachycardia and indicating the calculated position of the hands;

read from the memory 3-5 the video representing the sequence of hand movements for the cardiopulmonary resuscitation;

generate the driving signal S_pl further carrying the cardiopulmonary resuscitation video.

In one embodiment the position wherein to apply the hands on the chest of the human body is calculated as a function of the width x of the shoulders of the human body considered, so that the hands are positioned on the sternum of the analysed human body. In particular, a calculation is performed of the first distance y1 from the extremity of the right shoulder on which to apply the first electrode 2-1 and from the extremity of the left shoulder on which to apply the second electrode 2-2, a first straight line is identified which joins the first electrode 2-1 with the second electrode 2-2, and lastly a second straight line is identified perpendicular to the first in a point situated about halfway in the distance between the first electrode 2-1 and the second electrode 2-2: the position wherein to apply the hands is on the second straight line and at a distance such as to be on the patient's sternum.

Therefore the screen 3-2 of the mobile electronic device 3 is configured to receive a driving signal S_pl and to display a graphic or textual indication representing the presence of a cardiocirculatory arrest, ventricular tachycardia or ventricular fibrillation.

For example, screen 3-2 displays a heart-shaped image which assumes the following configurations:

the heart-shaped image is switched off in case of absence of cardiocirculatory arrest, ventricular tachycardia and ventricular fibrillation;

the heart-shaped image is switched on and flashes with a low frequency in a case of presence of ventricular fibrillation;

the heart-shaped image is switched on and flashes with a medium frequency in a case of presence of ventricular tachycardia;

the heart-shaped image is switched on and flashes with an high frequency in a case of presence of cardiocirculatory arrest;

Alternatively, the heart-shaped image is switched on and flashes with a same frequency in a case of presence of ventricular fibrillation, or ventricular tachycardia or cardiocirculatory arrest.

Moreover, the screen 3-2 is configured to display an image representing the chest of the analysed human body, wherein said chest image further comprises a fourth positioning area representing the position wherein to apply the hands with the purpose of carrying out the cardio-pulmonary resuscitation procedure.

The electrocardiogram generating module 2-6.3 is configured to generate, as a function of the values of the first, of the second and of the third detecting signal $S1\_r$, $S2\_r$, $S3\_r$ (and possibly of the fourth measuring signal $S4\_r$), the electrocardiogram signal S_ecg carrying the tracks of the loads representing the electrocardiogram of the heart of the analysed human body.

In particular, the electrocardiogram signal S_ecg carries the values of the tracks of the first lead DI, of the second lead DII and of the third lead DIII of bipolar type.

Alternatively, the electrocardiogram signal S_ecg carries the values of the tracks of the unipolar leads aVR, aVL and aVF, wherein:

the lead aVR is generated as a function of the first detecting electrical signal $S1\_r$ generated by the first electrode 2-1;

the lead aVL is generated as a function of the second detecting electrical signal $S2\_r$ generated by the second electrode 2-2;

the lead aVL is generated as a function of the third detecting electrical signal $S3\_r$ generated by the third electrode 2-3.

The transceiver 2-5 of the portable electronic device 2 is configured to receive the electrocardiogram signal S_ecg and to generate therefrom the short-range radio signal $S1\_s\_rd$ carrying said information indicating the values of the tracks of the leads representing the electrocardiogram.

The transceiver 3-4 of the mobile electronic device 3 is configured to receive the short-range radio signal $S2\_r\_sd$ carrying data indicating the values of the tracks of the leads of the electrocardiogram and to generate therefrom the internal signal S_int carrying data indicating the values of the tracks of the leads representing the electrocardiogram.

The screen 3-2 of the mobile electronic device 3 is configured to receive the internal signal S_int and to display the values of the tracks of the leads representing the electrocardiogram.

Figure 2:
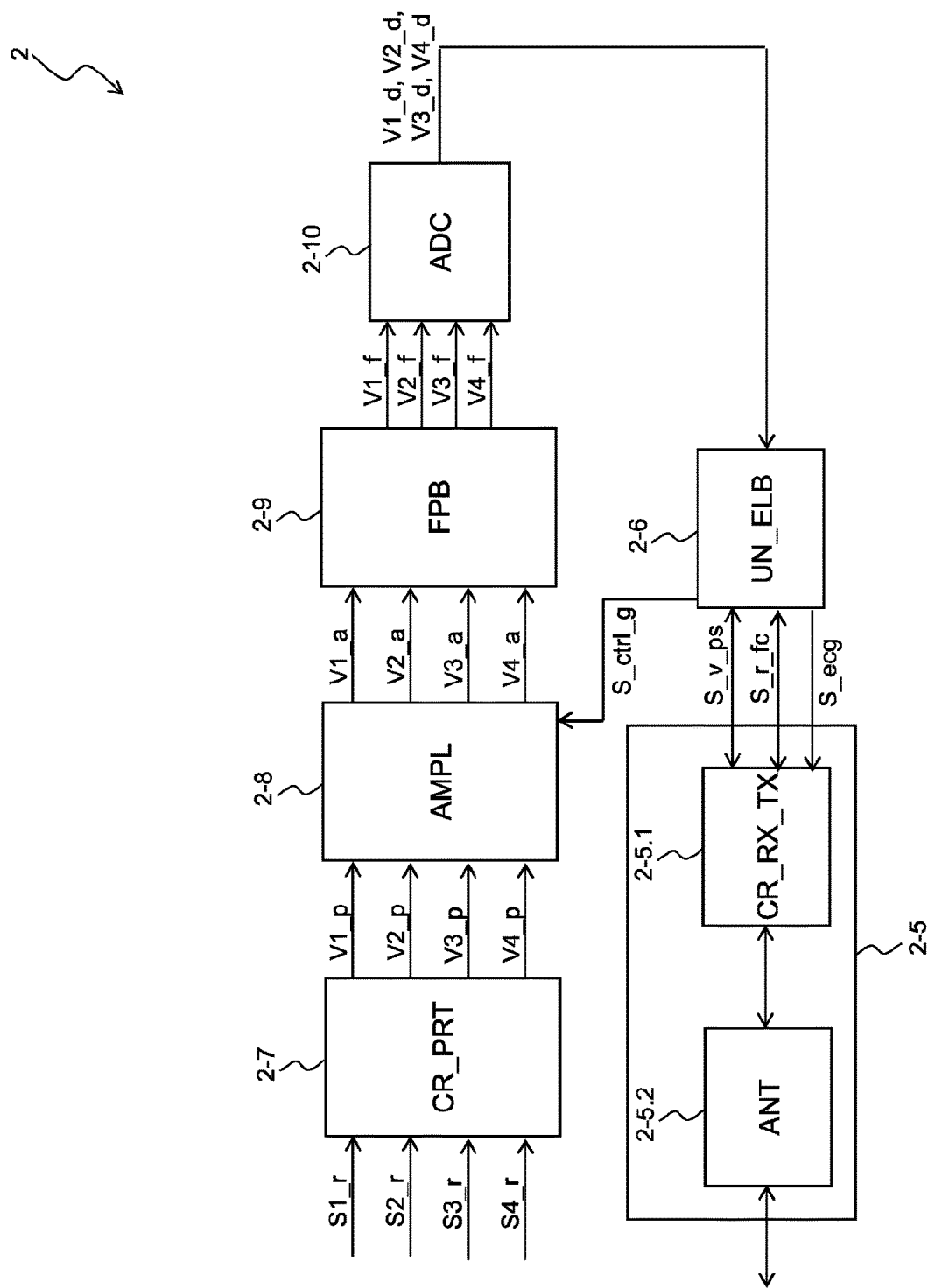
FIG. 2 shows in greater detail a portable electronic device used in the electronic system of FIG. 1.

With reference to FIG. 2, a block diagram of the portable electronic device 2 is shown in greater detail.

The portable electronic device 2 comprises a series connection of the following electronic components:

a protection circuit 2-7;

an amplification circuit 2-8;

a low-pass filter 2-9;

an analog-digital converter 2-10;

the processing unit 2-6;

a receiving/transmitting circuit 2-5.1;

an antenna 2-5.2.

The protection circuit 2-7 has the function of protecting the electronic circuits internally of the portable electronic device 2.

The protection circuit 2-7 comprises four input terminals adapted to receive the first, second, third and fourth detecting electrical signals $S1\_r$, $S2\_r$, $S3\_r$ e $S4\_r$ respectively which are signals of analog electrical voltage.

The protection circuit 2-7 further comprises four output terminals adapted to generate a first protected electrical voltage $V1\_pr$ calculated as a function of the first analog electrical voltage $S1\_r$, a second protected electrical voltage $V2\_pr$ calculated as a function of the second analog electrical voltage $S2\_r$, a third protected electrical voltage $V3\_pr$ calculated as a function of the third analog electrical voltage S3_r and a fourth protected electrical voltage V4_pr calculated as a function of the fourth analog electrical voltage S4_r, respectively.

The amplification circuit 2-8 has the function of amplifying the protected electrical voltage signals V1_pr, V2_pr, V3_pr, V4_pr.

The amplification circuit 2-8 further comprises four output terminals adapted to generate a first amplified electrical voltage V1_a calculated by means of the amplification of the value of the first protected electrical voltage V1_pr, a second amplified electrical voltage V2_a calculated by means of the amplification of the value of the second protected electrical voltage V2_pr, a third amplified electrical voltage V3_a calculated by means of the amplification of a value of the third protected electrical voltage V3_pr and a fourth amplified electrical voltage V4_a calculated by means of the amplification of the value of the fourth protected electrical voltage V4_pr, respectively.

Advantageously, the amplification circuit 2-8 comprises a further input terminal adapted to receive the gain control signal S_ctrl_g for regulating the gain value of the amplification circuit 2-8.

The processing unit 2-6 is configured to calculate the values of the first lead DI, of the second lead DII and of the third lead DIII, as explained in the foregoing.

In particular, the electrodes placement verification module 2-6.1 is further configured to adjust the value of the gain control signal S_ctrl_g as a function of the values of the first potential difference of the first lead DI, of the second potential difference of the second lead DII and of the third potential difference of the third lead DIII: in this way an adjustment of the values of the amplified electrical voltage signals V1_a, V2_a, V3_a, V4_a is performed and then it is performed a compensation of the difference of voltage values detected by the various electrodes 2-1, 2-2, 2-3.

The analog-digital converter 2-10 has the function of carrying out a conversion from analog to digital of the values of the first, second, third and fourth amplified electrical voltage V1_a, V2_a, V3_a, V4_a.

The analog-digital converter 2-10 comprises one or more output terminals adapted to generate a first digital electrical voltage V1_d calculated by means of the conversion from analog to digital of the value of the first amplified electrical voltage V1_a, a second digital electrical voltage V2_d calculated by means of the conversion from analog to digital of the value of the second amplified electrical voltage V2_a, a third digital electrical voltage V3_d calculated by means of the conversion from analog to digital of the value of the third amplified electrical voltage V3_a and a fourth digital electrical voltage V4_d calculated by means of the conversion from analog to digital of the value of the fourth amplified electrical voltage V4_a.

The processing unit 2-6 comprises one or more input terminals adapted to receive the values of the first, second, third and fourth digital electrical voltage V1_d, V2_d, V3_d, V4_d and to generate, as a function thereof, the positioning verification signal S_v_ps, the heart rate detection signal S_r_fc and the electrocardiogram S_ecg signal, as explained in the foregoing.

The set of the receiving/transmitting circuit 2-5.1 and of the antenna 2-5.2 constitutes the transceiver 2-5.

With reference to FIGS. 4A-4D, the flow chart 100 of the method for controlling the acquisition of an electrocardiogram according to the disclosure is shown.

Note that steps 102, 103, 104, 105, 106, 140, 141, 142, 132, 133, 135, 136, 149, 150, 151, 152, 153, 154, 155, 156, 157, 158 are performed on the processing unit 3-3 of the mobile electronic device 3.

Steps 107, 108, 109, 143, 144, 145, 130, 131, 147, 148 are instead performed on the processing unit 2-6 of the portable electronic device 2.

The flow diagram 100 begins with step 101.

Step 101 is followed by step 102 wherein the user of the mobile electronic device 3 (which can be the patient) selects the operation mode of the mobile electronic device 3, which can be one of the following:

"monitoring" operation mode, wherein it is performed an electrocardiogram of the patient's heart who is in a stable physical state, i.e. he is not complaining of acute cardiovascular symptoms;

"emergency" operation mode, wherein it is performed an electrocardiogram of the patient's heart who is in a cardiovascular symptomatic status, i.e. he is complaining of acute cardiovascular symptoms.

If the monitoring operation mode is selected, step 102 is followed by step 103, while if the emergency operation mode is selected, step 102 is followed by step 140.

First the monitoring mode will be described, followed by the emergency mode.

The monitoring mode comprises steps 103-110, 130-136.

In step 103 it is verified whether it is the first time the electronic system 1 is used:

in the affirmative case, it proceeds to step 104;
in the negative case, it proceeds to step 105.

In step 104 the configuration data of the patient are entered, as for example the name, the age, the sex.

Step 104 is followed by step 105 wherein a plurality of real-time images $I_1, I_2, \ldots I_n$ are acquired of the chest, shoulders, abdomen and pelvis of the patient.

Step 105 is followed by step 106 wherein a guide to the placement of the electrodes on the chest is carried out, as illustrated in the foregoing with the electrodes placement guiding module 3-3.1; therefore the image of FIG. 3A is displayed on the screen 3-2 of the mobile electronic device, which image shows the positioning area A1, A2, A3 (and possibly A4) wherein to place the electrodes 2-1, 2-2, 2-3 (and possibly 2-4) respectively.

The electrodes 2-1, 2-2, 2-3 (and possibly 2-4) are then positioned on the patient's chest.

Step 106 is followed by step 107 wherein it starts the acquisition of the electrical signals detected by the electrodes 2-1, 2-2, 2.3 and possibly 2-4.

Step 107 is followed by step 108 wherein it is verified the placement of the electrodes 2-1, 2-2, 2-3 on the patient's chest.

Step 108 is followed by step 109 wherein it is verified the correct placement of the electrodes 2-1, 2-2, 2-3 on the patient's chest, as illustrated in the foregoing with the electrodes placement verification module 2-6.1; therefore it is verified that the algebraic sum of the leads DI, DII, DIII is zero (or differs from zero for a value smaller than the sufficiently small tolerance value ε).

If the verification is positive (i.e. electrodes 2-1, 2-2, 2-3 have been correctly positioned on the chest), step 109 is followed by step 130.

If the verification is negative (i.e. electrodes 2-1, 2-2, 2-3 have not been correctly positioned on the chest), step 109 is followed by step 110.

In step 110 the electrodes 2-1, 2-2, 2-3 are removed from the respective positions wherein they were applied on the patient's skin and a return is performed to step 105.

Therefore the cycle composed of steps 105, 106, 107, 108, 109, 110 is repeated up to when it is detected that at least one of the electrodes 2-1, 2-2, 2-3 has been positioned correctly on the patient's chest.

In step 130 the electrical signals detected by the electrodes 2-1, 2-3, 2-3 (and possibly 2-4) are acquired and, as a function thereof, the electrocardiogram tracks of the patient's heart are generated.

Step 130 is followed by step 131 wherein the portable electronic device 2 transmits the short-range radio signal S1_r_sd carrying data representing the electrocardiogram tracks.

Step 131 is followed by step 132 wherein the portable electronic device 3 receives the short-range radio signal S2_r_sd carrying data representing the electrocardiogram tracks; further, the screen 3-2 of the mobile electronic device 3 displays the electrocardiogram tracks, as illustrated in FIG. 3C.

The tracks displayed on the screen 3-2 can be the bipolar leads DI, DII, DIII, or can be the unipolar leads aVR, aVL, aVF.

Step 132 is followed by step 133 wherein it is verified whether the function of measuring clinical parameters of the electrocardiogram on the mobile electronic device 3 has been selected:
- in the affirmative case (i.e. the measuring of the clinical parameters has been selected), it continues to step 135;
- in the negative case (i.e. the measuring of the clinical parameters has not been selected), it continues to step 134 wherein the flow chart 100 terminates.

Therefore the mobile electronic device 3 allows the measurement of the clinical parameters to be performed on the tracks of the electrocardiogram, such as for example:
- measuring the time length between two successive R waves;
- measuring the amplitude of one or more R waves;
- measuring the time length of the PR interval;
- measuring the time length of the QRS complex;
- measuring the elevation or depression of the ST segment with respect to an isoelectric line;
- measuring the time length of the QT interval;
- calculating the number of heart beats per minute.

In step 135 it is selected at least one track of the electrocardiogram and it is measured at least one parameter of the at least one selected track.

The values of the measured clinical parameters are indicated together with the respective tracks of the leads: in this way the values measured can be correctly associated to the correct track for a correct medical assessment.

Step 135 is followed by step 136 wherein at least one selected electrocardiogram track and the values of the respective clinical parameters measured are stored into the memory 3-5.

In one embodiment in step 136 the at least one selected track and the values of the respective measured clinical parameters are transmitted across a communication network (for example a long-range communication network of a radio-mobile type), so as to be sent to a medical centre or to the patient's doctor.

The tracks (with the measured values of the clinical parameters) can be saved on a pdf format file, which can be stored locally into the memory 3-5 of the mobile electronic device 3 or it can be saved into a cloud space. Said pdf file can be sent remotely in any way, for example as an attachment to an email message.

The "emergency" mode comprises steps 140-159.

In step 140 the patient's symptom is entered for carrying out the electrocardiogram.

The symptom can be for example a pain originating in the chest, dizziness, palpitations, syncope or pre-syncope.

Step 140 is followed by step 141, wherein it is performed a guide to the placement of the electrodes on the chest.

Steps 141, 142, 143, 144, 145, 146, 147, 148, 149 correspond to steps 105, 106, 107, 108, 109, 110, 130, 131, 132 respectively of the "monitoring" mode, to which reference is made.

Step 149 is followed by step 150 wherein an automatic measuring of the clinical parameters of the electrocardiogram is performed.

The measured clinical parameters can be selected from the list indicated herein above for step 135, i.e:
- measuring the time length between two successive waves R;
- measuring the amplitude of one or more R waves;
- measuring the time length of the PR interval;
- measuring the time length of the QRS complex;
- measuring the elevation or depression of the ST segment with respect to an isoelectric line;
- measuring the time length of the QT interval;
- calculating the number of heart beats per minute.

Step 150 is followed by step 151 wherein the electrocardiogram tracks and the values of the respective measured clinical parameters are transmitted across a communication network (for example a long-range communication network of a radio-mobile type), so as to be sent to a medical centre or the patient's doctor.

Advantageously, in step 151 not only are the electrocardiogram tracks generated in the emergency mode transmitted (together with the values of the respective measured clinical parameters), but also the tracks of at least one electrocardiogram generated in the monitoring mode are transmitted: in this way a doctor is able to make a comparison between the two electrocardiogram tracks of the same patient and is able to readily detect the presence of a cardiovascular alteration.

In one embodiment in step 151 the information representing the type of symptom that has caused the acquisition of the electrocardiogram in the emergency mode is further transmitted: in this way the doctor receiving the electrocardiogram in the presence of the cardiovascular alteration has no further need to ask questions to the patient in order to know the symptom, and he is able to readily associate the track of an electrocardiogram to the corresponding symptom.

Step 151 is followed by step 152 wherein it is performed a measurement of the distance between two successive R waves and the respective amplitude value in a defined time interval.

Step 152 is followed by step 153 wherein it is verified whether anomalies have been detected in the values of the distance between two successive R waves and/or in the value of the respective amplitude:
- in the affirmative case (i.e. anomalies have been detected), it continues to step 154 to;
- in the negative case (i.e. no anomalies have been detected), it continues to step 134 wherein the flow chart 100 terminates.

The irregularities detected (and the detecting modes) are those illustrated in the foregoing in the description of the heart rate detecting module 2-6.2, i.e. cardiocirculatory arrest, ventricular fibrillation or ventricular tachycardia.

In step 154 the cardio-pulmonary resuscitation procedure starts, which terminates with step 159.

In step 154 a plurality of real-time images $I_1, I_2, \ldots I_n$ of the chest, shoulders, abdomen and pelvis of the patient are acquired.

Step 154 is followed by step 155 wherein it is performed a guide to the positioning of the hands on the chest, as illustrated in the foregoing with the hand placement guiding module 3-3.2; therefore an image of the patient's chest is displayed on the screen 3-2 of the mobile electronic device 3, which image shows the position wherein to apply the hands with the purpose of carrying out the cardio-pulmonary resuscitation procedure.

Step 155 is followed by step 156 wherein the video of the guided procedure to cardio-pulmonary resuscitation is read from the memory 3-5.

Step 156 is followed by step 157 wherein the screen 3-2 displays said video of the cardio-pulmonary resuscitation Step 157 is followed by step 158 wherein the cardio-pulmonary resuscitation on the patient is commenced by any person.

Step 158 is followed by step 158 wherein the flow chart 100 terminates.

In one embodiment between step 150 and step 151 there is a further step wherein it is performed the geolocalisation of the mobile electronic device 3 and the coordinates representing the geographic position wherein the mobile electronic device 3 is located on planet Earth are generated. For example, it is used a satellite localisation system of a GPS type and thus the GPS coordinates are obtained. Moreover, step 151 further comprises transmission across the communication network of the coordinates representing the geographical position wherein the mobile electronic device 3 is located. The information relating to the coordinates of the geographical position of the mobile electronic device 3 can be received by a medical centre which can call an ambulance, or can be received directly by a central emergency unit which sends an ambulance to the position wherein the patient is located, using the coordinates of the geographical position wherein the mobile electronic device 3 is located.

Figure 4A:
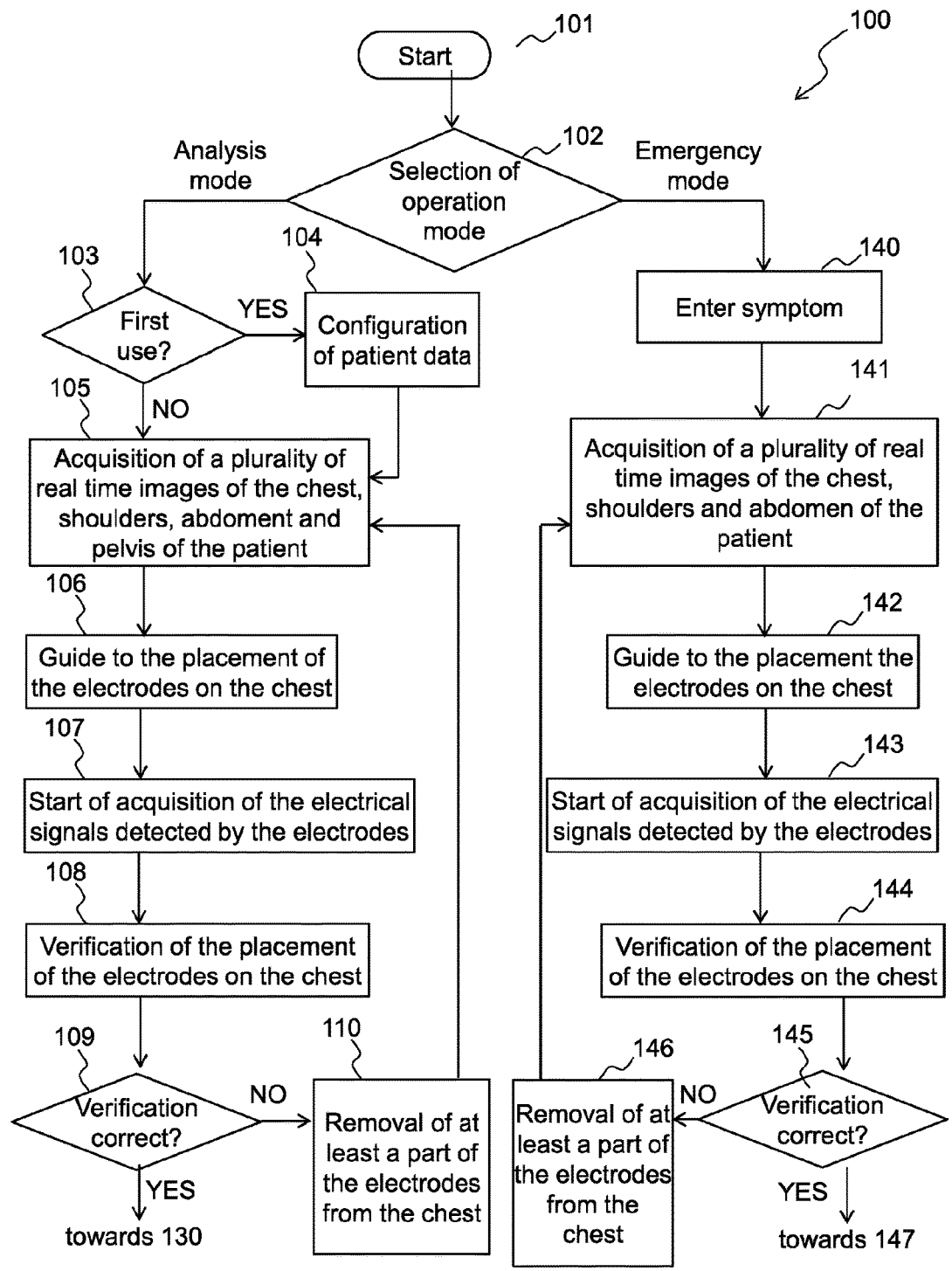
FIGS. 4A-4D show the flow diagram of the method for controlling the acquisition of an electrocardiogram according to the disclosure.
Figure 4B:
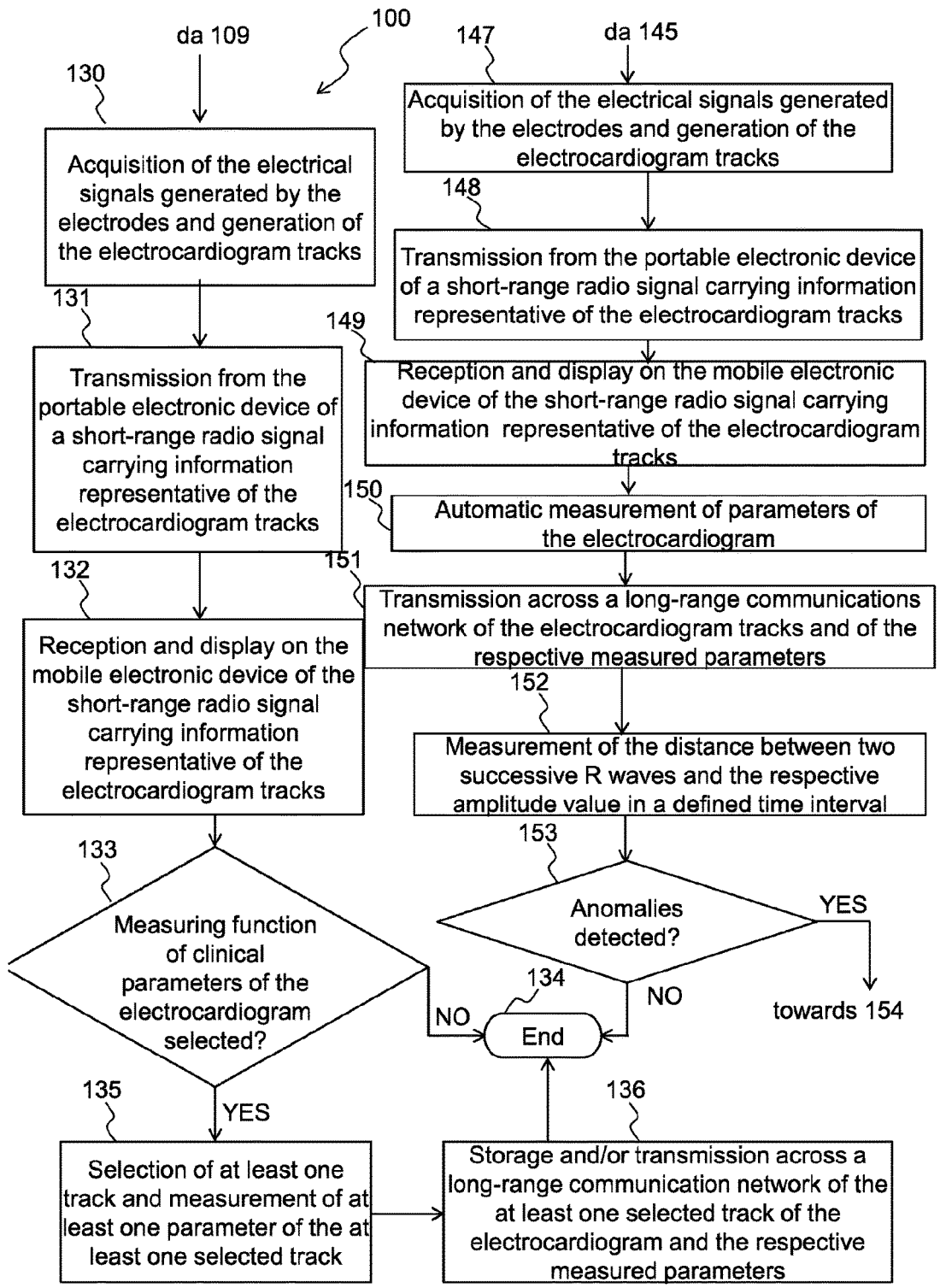
Figure 4C:
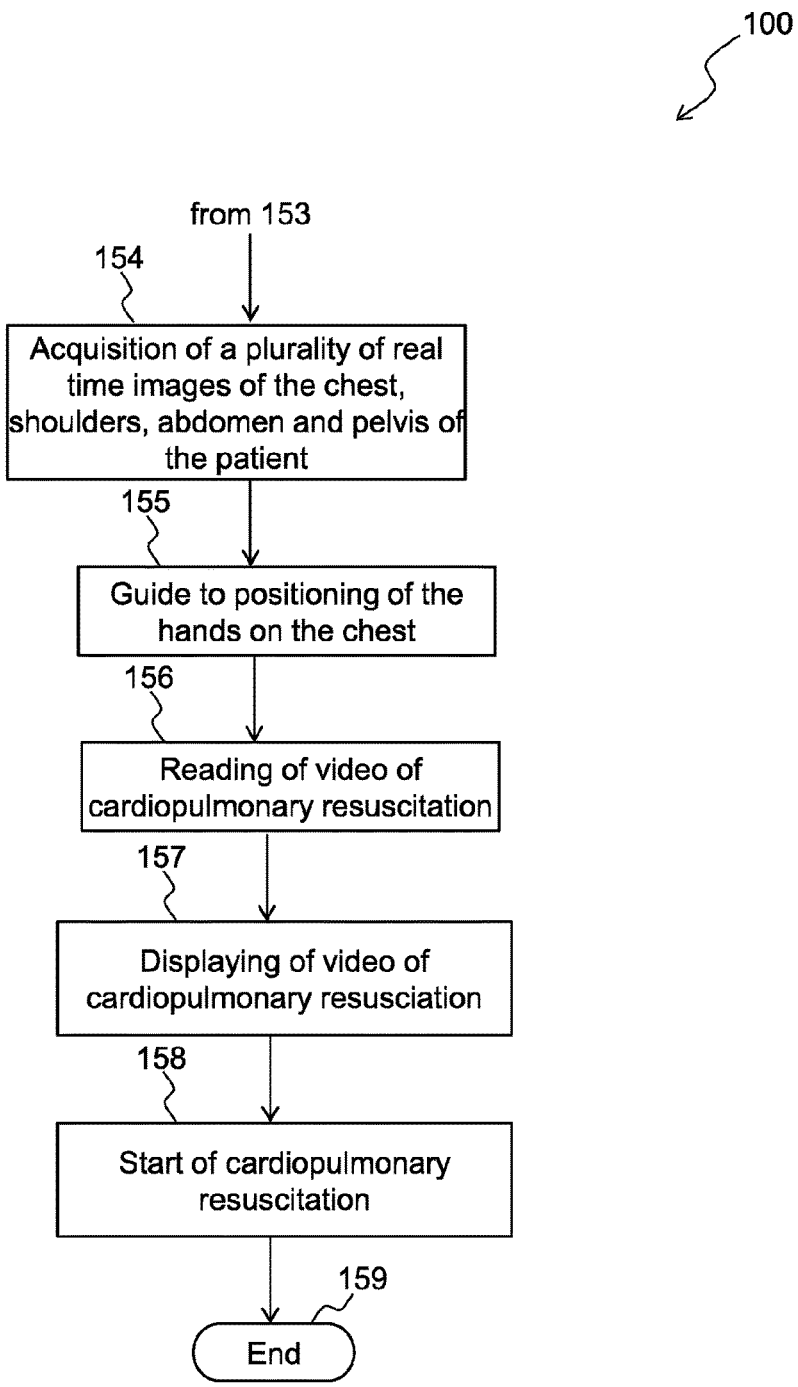
Figure 4D:
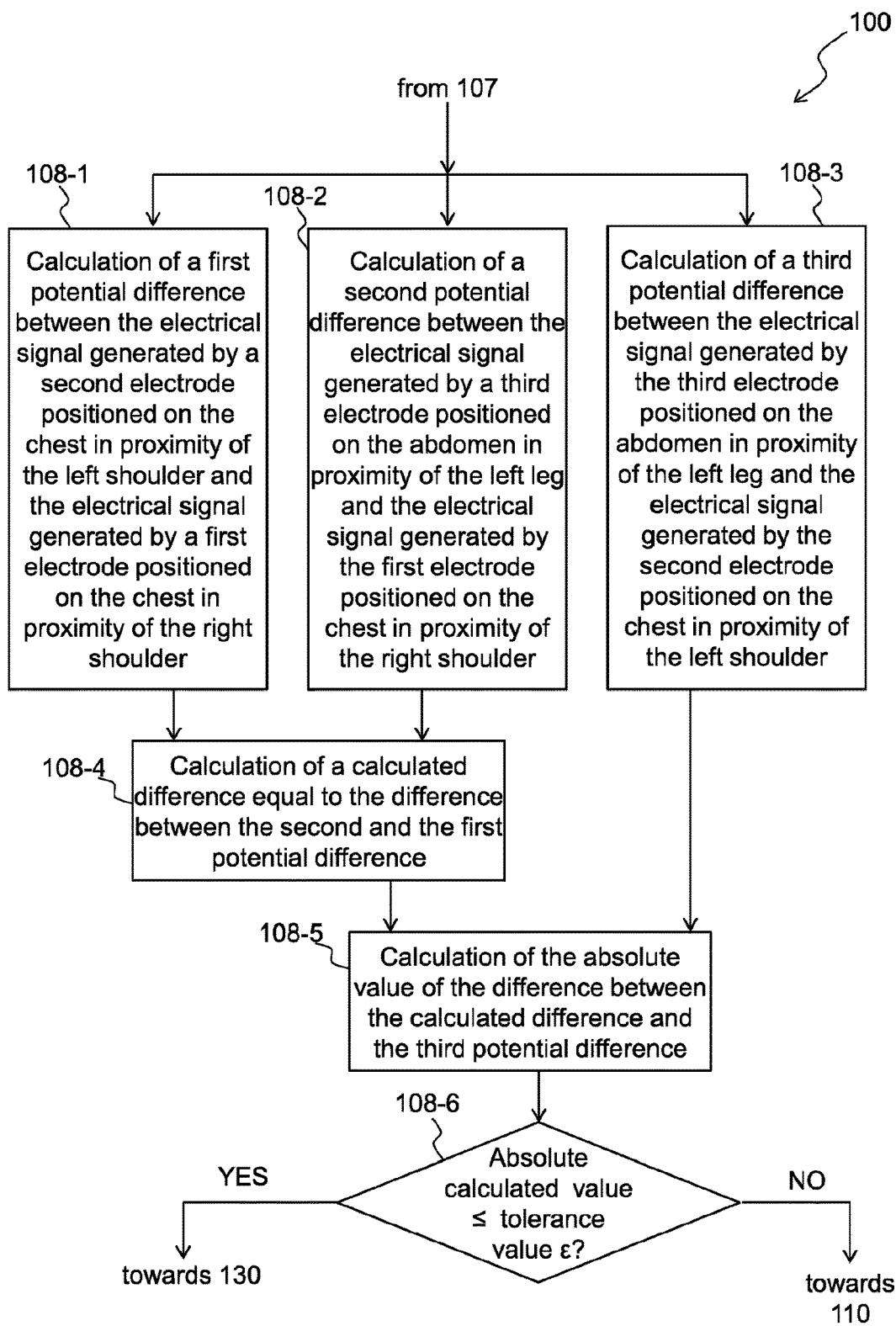

Advantageously, in steps 108-109 the verification of the correct placement of the electrodes is carried out in steps 108-1, 108-2, 108-3, 108-4, 108-5, 108-6 shown in FIG. 4D; note that said steps are performed in the electrodes placement verification module 2-6.1 illustrated in the foregoing.

In this case step 107 is followed in parallel by steps 108-1, 108-2, 108-3.

In step 108-1, it is calculated the first lead DI equal to a first potential difference between the electrical signal generated by the second electrode 2-2 positioned on the chest in proximity of the left shoulder and the electrical signal generated by the first electrode 2-1 positioned on the chest in proximity of the right shoulder.

In step 108-2, it is calculated the second lead DII equal to a second potential difference between the electrical signal generated by the third electrode 2-3 positioned on the abdomen in proximity of the left leg and the electrical signal generated by the first electrode 2-1 positioned on the chest in proximity of the right shoulder.

In step 108-3, it is calculated the third lead DIII equal to a third potential difference between the electrical signal generated by the third electrode 2-3 positioned on the abdomen in proximity of the left leg and the electrical signal generated by the second electrode 2-2 positioned on the chest in proximity of the left shoulder.

Steps 108-1 and 108-2 are followed by step 108-4 wherein a difference $\Delta_{II-I}$ is calculated that is equal to the difference between the second potential difference of the second lead DII and the first potential difference of the first lead DI.

Steps 108-3 and 108-4 are followed by step 108-5 wherein it is calculated an absolute value of the difference between the calculated difference $\Delta_{II-I}$ and the potential difference of the third lead DIII.

Step 108-5 is followed by step 108-6 wherein a verification is performed as to whether the absolute value calculated is lower than or equal to a tolerance value ε:
- in the positive case (i.e. the calculated absolute value is smaller than or equal to the tolerance value ε), it continues to step 130;
- in the negative case (i.e. the calculated absolute value is greater than the tolerance value ε), it continues to step 110.

A description will now be made of a first operation of the electronic system 1 in the monitoring operating mode, with reference also to FIGS. 1, 3A, 4A and 4B.

For the purposes of simplicity the following hypotheses are considered:
- the mobile electronic device 3 is a smartphone provided with a front camera 3-1 and a screen 3-2 of the touch-screen type;
- a first software application is installed on the mobile electronic device 3, which carries out steps 102, 103, 104, 105, 106, 132, 133, 135, 136, 135 of the flow chart 100;
- a second software application is run on the portable electronic device 2, which performs steps 107, 108, 109, 130, 131 of the flow chart 100;
- the patient himself carries out an electrocardiogram of his heart (i.e. performs a self-monitoring of the heart) and thus the user of the smartphone 3 is the patient himself.
- the portable electronic device 2 is used for the first time;
- four electrodes 2-1, 2-2, 2-3, 2-4 are used;
- the positioning areas A1, A2, A3, A4 have a circular shape;
- the short-range radio signal exchanged between the smartphone 3 and the portable electronic device is of the Bluetooth type.

At the initial instant t0 the patient has his chest uncovered and he starts the first software application on the smartphone 3.

Then the patient selects the monitoring operation mode (step 102) and selects the front camera 3-1.

The processing unit 3-3 detects that it is the first time the first software application has been used and thus it displays on the screen 3-2 a request for entry of the patient's configuration data.

At instant t1 (following t0) the patient enters his configuration data using the screen 3-2 of a touch-screen type, such as his name, age, address, gender.

At instant t2 (following t1) the processing unit 3-3 of the smartphone 3 activates the front camera 3-1 of the smartphone 3, thus the patient uses a hand to position the smartphone in order to frame his shoulders, chest, abdomen and pelvis.

The processing unit 3-3 performs step 105 and the camera 3-1 acquires a plurality of real-time images $I_1, I_2, \ldots I_n$ of the chest, shoulders, abdomen and pelvis of the patient (for example, 10 images)

Subsequently the processing unit 3-3 performs step 106 and the screen 3-2 shows the real-time image of the patient's chest which shows four positioning areas A1, A2, A3, A4 wherein to position electrodes 2-1, 2-2, 2-3, 2-4 respectively, as illustrated in FIG. 3A.

At instant t3 (following t2) the patient positions electrode 2-1 on the skin of the chest externally of the positioning area A1 which is in proximity of the right shoulder, positions electrode 2-2 on the skin of the chest inside the positioning area A2 which is in proximity of the left shoulder, positions electrode 2-3 on the skin of the pelvis inside the positioning area A3 which is in proximity of the left leg and positions electrode 2-4 on the skin of the pelvis inside the positioning area A4 in proximity of the right leg.

At instant t4 (following t3) the processing unit 2-6 of the portable electronic device 2 detects the presence of the electrodes 2-1, 2-2, 2-3, 2-4 on the patient's skin and performs step 107 wherein it starts to acquire the electrical signals $S1\_r$, $S2\_r$, $S3\_r$, $S4\_r$ generated by the electrodes 2-1, 2-2, 2-3, 2-4 respectively.

Subsequently the processing unit 2-6 performs steps 108, 109 wherein it performs the verification of the correct placement of the electrodes 2-1, 2-2, 2-3 on the patient's chest; in particular the processing unit 2-6 detects that at least one electrode has not been positioned correctly, because the electrode 2-1 has been positioned externally of the positioning area A1.

Therefore the screen 3-2 displays a flashing text message indicating that at least one electrode has not been correctly positioned.

Therefore the patient observes the screen 3-2, notes the flashing text message and removes the electrode 2-1 from the skin (step 110).

At instant t5 (following t4) the processing unit 3-3 performs again steps 105 and 106 and the screen 3-2 shows again the real-time image of the patient' chest which shows four positioning areas A1, A2, A3, A4 wherein to position electrodes 2-1, 2-2, 2-3, 2-4 respectively.

In instants comprised between t6 (following t5) and t7 (excluded) the operation is similar to that explained in the foregoing at instants t3 and t4, with the difference that the patient positions electrode 2-1 on the skin of the chest inside the positioning area A1 which is in proximity of the right shoulder; consequently, the processing unit 2-6 detects that the electrodes 2-1, 2-2, 2-3 are positioned correctly and the screen 3-2 displays a text message indicating the correct placement.

At instant t7 (following t6) the portable electronic device 2 acquires the electrical signals $S1\_r$, $S2\_r$, $S3\_r$, $S4\_r$ detected by the electrodes 2-1, 2-3, 2-3, 2-4 respectively and generates the electrocardiogram tracks of the patient's heart (step 130).

Subsequently, the portable electronic device 2 transmits via Bluetooth towards the smartphone 3 the signal $S1\_r\_sd$ carrying information representing the electrocardiogram tracks (step 131).

At instant t8 (following t7) the smartphone 3 receives, via Bluetooth, signal $S2\_r\_sd$ carrying information representing the electrocardiogram tracks (step 132) and it displays the electrocardiogram tracks on the screen 3-2, as illustrated in FIG. 3C.

Subsequently, the patient does not carry out any measurement of the clinical parameters of the electrocardiogram (steps 133 and 134).

A description will now be made of a second operation of the electronic system 1, operating in the emergency mode, with reference also to FIGS. 1, 3A, 4A, 4B, 4C.

Consider the same hypotheses of the first operation mode, with the following differences:
the rear camera 3-1 is used;
the patient is aided by a family member;
the family member carries out the electrocardiogram on the patient, thus the user of the smartphone 3 is the family member;

At the initial instant t10 the patient detects a cardiovascular symptom, uncovers his/her chest and starts the first software application on the smartphone 3.

Then the family member selects the emergency operation mode (step 102) and selects the rear camera 3-1 and enters the patient's symptom (step 140).

In the instants comprised between t11 (following t10) and t12 (excluded), the operation is the same as for that described previously between instants t6 and t8, i.e. steps 141, 142, 143, 144, 145, 147, 148, 149 of the flow chart 100 are performed.

At instant t12 (following t11) the smartphone 3 performs an automatic measurement of the clinical parameters of the electrocardiogram (step 150) and transmits the electrocardiogram tracks (and the values of the respective clinical parameters measured) via a radio-mobile network to a medical centre (step 151).

Moreover, the processing unit 3-3 of the smartphone 3 carries out a measurement of the distance between two successive waves R of a track of the electrocardiogram and detects the presence of heart anomalies (step 153 and transition from step 153 to step 154); in particular the presence of a cardiocirculatory arrest of the patient's heart is detected.

In the instants comprised between t13 (following t12) and t14 (excluded) the smartphone 3 performs steps 154, 155, 156, 157 and thus the screen 3-2 displays first the image of the patient's chest which shows the position wherein to apply the hands with the purpose of carrying out the cardio-pulmonary resuscitation procedure and then the video of the guided cardio-pulmonary resuscitation procedure.

The family member applies hisr hands on the patient's chest in the indicated position on the screen 3-2 and performs the cardio-pulmonary resuscitation procedure, following the instructions of the video on the screen 3-2, alternating strikes on the sternum with pauses.

At instant t14 (following t13) the patient's heart recommences beating and thus the patient has been saved.

According to a first aspect, it is also an object of the present disclosure a method for controlling acquisition of an electrocardiogram, wherein said method is run on the control unit of the portable electronic device 2.

The method comprises the steps of:
a) generating a first, a second and a third detecting electrical signal representing the current generated on the skin by the activity of the heart of a human being in the points wherein a first, a second and a third electrode are positioned respectively on a portion of the human body;
b) calculating a first lead DI equal to a first potential difference between the second detecting electrical signal $S2\_r$ and the first detecting electrical signal $S1\_r$;
c) calculating a second lead DII equal to a second potential difference between the third detecting electrical signal $S3\_r$ and the first detecting electrical signal $S1\_r$;
d) calculating a third lead DIII equal to a third potential difference between the third detecting electrical signal $S3\_r$ and the second detecting electrical signal $S2\_r$;
e) calculating a difference equal to the difference between the second and the first potential difference;
f) verifying whether the absolute value of the difference between the calculated difference and the third potential difference is smaller than a tolerance value;
g) in case of a positive verification, detecting the correct placement of the first, second and third electrode;

h) in case of a negative verification, detecting an incorrect placement of at least one electrode among the first, second and third electrode.

It is also an object of the present disclosure a computer program comprising software code portions adapted to perform the steps b)-h) of the method according to the first aspect, when said program is run on at least one computer.

According to a second aspect, it is also an object of the present disclosure a method for controlling acquisition of an electrocardiogram, wherein said method is run on the control unit of the mobile electronic device 3.

The method comprises the steps of:
a) receiving a plurality of real-time images representing a portion of the human body;
b) identifying a feature of the portion of the human body within said plurality of images;
c) calculating, as a function of the identified feature, the position wherein to apply the first, second and third electrodes on the portion of the human body;
d) displaying a real-time image representing said portion of the human body and further comprising a first positioning mark A1, a second positioning mark A2 and a third positioning mark A3 representing the positions wherein to apply the first, the second and the third electrode respectively.

In one embodiment in the method of the second aspect:
step a) comprises receiving the plurality of real-time images representing the shoulders, the chest, the abdomen and the pelvis of the human body,
step b) comprises identifying the position of the shoulders within at least part of said plurality of images,
step c) comprises:
c1) calculating the width x of the shoulders as a function of at least part of said plurality of images;
c2) calculating, as a function of the width x of the shoulders and the value of a first parameter k, a first distance y1 between the first positioning area and the extremity of the right shoulder and between the second positioning area and the extremity of the left shoulder;
c3) calculating the width z of the pelvis;
c4) calculating, as a function of the width z of the pelvis and of the value of a second parameter r, a second distance t1 between the third positioning area and the extremity of the left pelvis;
c5) calculating a third distance h between the third positioning area and the first positioning area equal to a value comprised in a range centred on half the width x of the shoulders;
step d) comprises displaying the real-time image representing at least the chest of the human body and further comprises:
the first positioning mark consisting of a first positioning area A1 wherein to apply the first electrode 2-1 positioned on the chest in proximity to the left shoulder and having a position identified by the first distance;
the second positioning mark consisting of a second positioning area A2 wherein to apply the second electrode 2-2 positioned on the chest in proximity to the right shoulder and having a position identified by the first distance;
the third positioning mark consisting of a third positioning area A3 wherein to apply the third electrode (2-3) positioned on the abdomen in proximity to the left leg and having a position identified by the third distance and by the fourth distance.

It is also an object of the present disclosure a computer program comprising software code portions adapted to perform the steps of the method according to the second aspect, when said program is run on at least one computer.

It is also an object of the present disclosure a portable electronic device 2 to control the acquisition of an electrocardiogram.

The portable electronic device further comprises:
a first electrode 2-1, a second electrode 2-2 and a third electrode 2-3 configured to generate a first detecting electrical signal $S1\_r$, a second detecting electrical signal $S2\_r$ and a third $S3\_r$ detecting electrical signal respectively representing the current generated on the skin by the activity of the heart of a human being in the respective points wherein the first, second and third electrodes are positioned on said portion of the human body;
a transceiver 2-5 of short-range radio signals;
a processing unit 2-6 connected with the transceiver 2-5 and with the first electrode 2-1, second electrode 2-2 and third electrode 2-3;

The processing unit 2-6 of the portable electronic device comprises a module 2-6.1 for verifying the placement of the first, second and third electrodes, wherein said electrodes placement verification module is configured to:
receive the first, second and third detecting electrical signals generated by the first, second and third electrodes respectively;
calculate a first lead DI equal to a first potential difference between the second detecting electrical signal $S2\_r$ and the first detecting electrical sensing signal $S1\_r$;
calculate a second lead DII equal to a second potential difference between the third detecting electrical signal $S3\_r$ and the first detecting electrical signal $S1\_r$;
calculate a third lead DIII equal to a third potential difference between the third detecting electrical signal $S3\_r$ and the second detecting electrical signal $S2\_r$;
calculate a difference equal to the difference between the second and the first potential difference;
verify whether the absolute value of the difference between the calculated difference and the third potential difference is lower than a tolerance value;
in case of a positive verification, generate a positioning verification signal $S\_v\_ps$ indicating the correct placement of the first, second and third electrodes;
in case of a negative verification, generate a positioning verification signal $S\_v\_ps$ indicating the incorrect placement of at least one electrode between the first and third electrodes.

The transceiver 2-5 of the portable electronic device 2 is configured to receive the positioning verification signal and generate therefrom a short-range radio signal $S1\_s\_rd$ carrying information indicating the correct placement of the first, second and third electrodes or indicating the incorrect placement of at least one electrode among the first, second and third electrodes.

The present disclosure also relates to a mobile electronic device 3, in particular a smartphone for controlling the acquisition of an electrocardiogram.

The portable electronic device further comprises:
an optical device 3-1 for acquiring real-time images of a portion of a human body;
a screen 3-2;
a processing unit 3-3 connected with the optical device and with the screen.

The processing unit 3-3 of the mobile electronic device comprises an electrodes placement guiding module 3-3.1 for the first, second and third electrodes, wherein the electrode placement guiding module is configured to:
   receive a plurality of real-time images representing a portion of the human body;
   identify a feature of the portion of the human body within at least part of said plurality of images;
   calculate, as a function of the identified characteristic, the positions wherein to apply the first, second and third electrodes on the portion of the human body;
   generate a driving signal S_pl carrying information indicating the calculated positions wherein to apply the first, second and third electrodes;
   Moreover, the screen 3-2 is configured to:
   receive said driving signal S_pl;
   display a real-time image representing said portion of the human body and further comprising a first positioning mark A1, a second positioning mark A2 and a third positioning mark A3 representing the positions wherein to apply the first, second and third electrodes respectively.

The invention claimed is:
1. An electronic system to control the acquisition of an electrocardiogram, the system comprising a portable electronic device and a mobile electronic device,
   the mobile electronic device comprising:
      an optical device for acquiring real-time images of a portion of a human body;
      a screen;
      a processing unit connected to the optical device and to the screen;
   the portable electronic device comprising:
      a first, a second and a third electrode configured to generate, respectively, a first, a second and a third detecting electrical signal representing a current generated on the skin by the activity of the heart of a human being in the respective points wherein the first, second, and third electrodes are positioned on said portion of the human body;
   the processing unit of the mobile electronic device comprising an electrodes placement guiding module for the first, second, and third electrode, wherein the electrodes placement guiding module is configured to:
      receive a plurality of real-time images representing the portion of the human body;
      identify a feature of the portion of the human body within at least part of said plurality of images;
      calculate, as a function of the identified feature, the positions on which to apply the first, second and third electrode on the portion of the human body; and
      generate a driving signal carrying information indicating the calculated positions on which to apply the first, second and third electrode;
   wherein the screen is configured to:
      receive said driving signal; and
      display a real-time image representing said portion of the human body and further comprising a first positioning mark, a second positioning mark and a third positioning mark representing the positions to apply the first, second and third electrode respectively.
2. The electronic system according to claim 1, wherein:
   the portion of the human body comprises shoulders, a chest, an abdomen and a pelvis;
   the first positioning mark is a first positioning area in which the first electrode is to be applied and wherein the first positioning mark is positioned on the chest in proximity to the left shoulder;
   the second positioning mark is a second positioning area in which the second electrode is to be applied and wherein the second positioning mark is positioned on the chest in proximity to the right shoulder;
   the third positioning mark is a third positioning area in which the third electrode is to be applied and wherein the third positioning mark is positioned on the abdomen in proximity to the left leg;
   the feature of the portion of the human body is one of the two shoulders;
   and
   wherein said electrodes placement guiding module is configured to:
   receive the plurality of real-time images representing the shoulders, the chest, the abdomen and the pelvis;
   identify the position of the shoulders within at least part of said plurality of images;
   calculate the width of the shoulders as a function of at least part of said plurality of images;
   calculate, as a function of the width of the shoulders and of a value of a first parameter, a first distance between the first positioning area and an extremity of the right shoulder and between the second positioning area and an extremity of the left shoulder;
   calculate the width of the pelvis;
   calculate, as a function of the width of the pelvis and of a value of a second parameter, a second distance between the third positioning area and an extremity of the left pelvis;
   calculate a third distance between the third positioning area and the first positioning area equal to a value comprised in a range centered on half the width of the shoulders;
   generate the driving signal carrying information indicating the first, second and third distance;
   wherein the screen is configured to receive the driving signal and display the real-time image representing at least the chest of the human body, wherein said image comprises:
   the first and the second positioning areas having a position identified by the first distance;
   the third positioning area having a position identified by the third distance and by the fourth distance.
3. The electronic system according to claim 2,
   wherein the mobile electronic device further comprises a transceiver of short-range radio signals connected to the processing unit,
   wherein the portable electronic device further comprises:
      a transceiver of short-range radio signals; and
      a processing unit connected to the transceiver and to the first, the second, and the third electrode;
   the processing unit of the portable electronic device comprising a verification module of the placement of the first, second, and third electrode, wherein said verification module of the electrodes placement is configured to:
      receive the first, second, and third detecting electrical signals generated by, respectively, the first, second and third electrodes;
      calculate a first lead equal to a first potential difference between the second detecting electrical signal and the first detecting electrical signal;
      calculate a second lead equal to a second potential difference between the third detecting electrical signal and the first detecting electrical signal;

calculate a third lead equal to a third potential difference between the third detecting electrical signal and the second detecting electrical signal;

calculate a difference equal to the difference between the second and the first potential difference;

verify whether the absolute value of the difference between the calculated difference and the third potential difference is smaller than a tolerance value;

in case of a positive verification, generate a positioning verification signal indicating the correct placement of the first, second, and third electrode;

in case of a negative verification, generate the positioning verification signal indicating the, incorrect placement of at least one electrode among the first, second and third electrode;

wherein the transceiver of the portable electronic device is configured to receive the positioning verification signal and generate therefrom a short-range radio signal carrying information indicating the correct placement of the first, second, and third electrode or indicating the incorrect placement of at least one electrode among the first, second, and third electrode, wherein the transceiver of the mobile electronic device is configured to receive a short-range radio signal carrying said information indicating the correct or incorrect placement and generate therefrom an internal signal carrying said information indicating the correct or incorrect placement, and wherein the screen of the mobile electronic device is configured to receive the internal signal and display a graphical or textual indication representing the correct placement of the first, second, and third electrode or indicating the incorrect placement of at least one electrode among the first, second, and third electrode.

4. The electronic system according to claim 1, wherein the processing unit of the portable electronic device further comprises a heart rate detecting module configured to:

receive the first, second, and third detecting electrical signal and measure, as a function thereof, a distance between two subsequent R waves and the respective amplitude value in a defined time interval;

if the amplitude value of the R waves is smaller than the value of a first amplitude threshold, generate a heart rate detecting signal having a first value indicating the presence of a cardio-circulatory arrest of the heart of the human body;

if the amplitude value of the R waves is comprised between the value of the first amplitude threshold and the value of a second amplitude threshold greater than the first amplitude threshold and if the value of said distance is smaller than the value of a first distance threshold, generate the heart rate detecting signal having a second value indicating the presence of a ventricular fibrillation of the heart of the human body;

if the value of said distance is comprised between the value of the first distance threshold and the value of a second distance threshold greater than the first distance threshold, generate the heart rate detecting signal having a third value indicating the presence of a ventricular tachycardia of the heart of the human body;

wherein the transceiver of the portable electronic device is configured to receive the heart rate detecting signal and generate therefrom the short-range radio signal carrying information indicating the presence of the cardiocirculatory arrest, the ventricular fibrillation or the ventricular tachycardia, wherein the transceiver of the mobile electronic device is configured to receive a short-range radio signal carrying said information indicating the presence of the cardiocirculatory arrest, the ventricular fibrillation or the ventricular tachycardia and generate therefrom an internal signal carrying said information indicating the presence of the cardiocirculatory arrest, the ventricular fibrillation or the ventricular tachycardia, wherein the mobile electronic device comprises a memory for storing a video representing a guided procedure for cardiopulmonary resuscitation, said video containing a sequence of images representing the position of the hands to be applied on the sternum of the human body and the timing of the pressures exerted by the hands on the sternum, the processing unit of the mobile electronic device comprising a hand placement guiding module configured to:

receive the information indicating the presence of the cardiocirculatory arrest, the ventricular fibrillation or the ventricular tachycardia;

receive the plurality of real-time images representing at least the chest of the human body;

identify said feature of the portion of the human body within said plurality of images;

calculate, as a function of the identified feature, the position on which to apply the first and the second electrode on the chest of the human body;

calculate, as a function of the calculated position of the first and second electrode, the position on which to apply the hands on the chest of the human body in order to perform a sequence of hand movements for a cardiopulmonary resuscitation of the heart of the human body;

generate the driving signal indicating the presence of the cardiocirculatory arrest, the ventricular fibrillation or the ventricular tachycardia and indicating the calculated position of the hands;

read from the memory the video representing the sequence of hand movements for the cardiopulmonary resuscitation;

generate the driving signal that includes the cardiopulmonary resuscitation video;

wherein the screen of the mobile electronic device is configured to:

receive the driving signal;

display a graphical or textual indication representing the presence of a cardiocirculatory arrest, ventricular tachycardia or ventricular fibrillation;

display an image representing the chest of the human body and further comprising a fourth positioning area representing a position on which to apply the hands;

display said cardiopulmonary resuscitation video.

5. The electronic system according to claim 3, wherein the portable electronic device comprises an amplification circuit having a gain variable as a function of a gain control signal, the amplification circuit being configured to receive the first, second, and third detecting electrical signals and generate therefrom, respectively, first, second, and third amplified signals, wherein the electrodes placement verification module is further configured to regulate a value of the gain control signal as a function of the values of the first, second, and third potential difference.

6. The electronic system according to claim 1, wherein the processing unit of the portable electronic device further comprises an electrocardiogram generating module configured to generate an electrocardiogram signal carrying the values of the tracks of a first electrocardiogram of a patient in a stable physical state and of a second electrocardiogram of the patient having cardiovascular symptoms, wherein the transceiver of the portable electronic device is configured to receive the electrocardiogram signal and generate therefrom the short-range radio signal carrying said information indicating the values of the tracks of the first and second electrocardiograms and carrying information indicating the symptom associated with the second electrocardiogram, wherein the transceiver of the mobile electronic device is configured to receive a short-range radio signal carrying said information indicating the values of the tracks of the first and second electrocardiograms and carrying information indicating said symptom, wherein the screen of the mobile electronic device is configured to display the tracks of the first or of the second electrocardiogram, and wherein the mobile electronic device further comprises a long-range radio signal transceiver configured to transmit to a medical center or to a central emergency unit for ambulance management a long-range radio signal carrying said information indicating the values of the tracks of the first and second electrocardiograms and carrying said information indicating the symptom associated with the second electrocardiogram.

7. The electronic system according to claim 1, wherein the screen is configured to display the tracks of at least three leads of the electrocardiogram on a single screenshot, wherein the mobile electronic device includes a camera and is selected from among the following:
        a smartphone;
        a tablet;
        a laptop;
    wherein the camera is positioned:
        on a front or a rear side of the smartphone;
        on a front side of the tablet;
        above a screen of the laptop;
    wherein the short-range radio signal is of the Bluetooth type.

8. The electronic system according to claim 2, wherein the shape of the first, of the second, and of the third positioning areas are selected from among the following:
    a first, second, and third rectangle which do not overlap each other, wherein the first rectangle is aligned with the second rectangle;
    a first, second, and third circle which do not overlap each other, wherein the first circle is aligned with the second circle.

9. A method for controlling an acquisition of an electrocardiogram, the method comprising:
    a) generating a first, a second, and a third detecting electrical signal representing a current generated on the skin by the activity of the heart of a human being in the points at which a first, a second, and a third electrode are positioned respectively on a portion of the human body;
    b) calculating a first lead equal to a first potential difference between the second detecting electrical signal and the first detecting electrical signal;
    c) calculating a second lead equal to a second potential difference between the third detecting electrical signal and the first detecting electrical signal;
    d) calculating a third lead equal to a third potential difference between the third detecting electrical signal and the second detecting electrical signal;
    e) calculating a difference equal to the difference between the second and the first potential difference;
    f) verifying whether an absolute value of the difference between the calculated difference and the third potential difference is smaller than a tolerance value;
    g) in case of a positive verification, detecting a correct placement of the first, second, and third electrode;
    h) in case of a negative verification, detecting an incorrect placement of at least one electrode among the first, second, and third electrode.

10. A method for controlling the acquisition of an electrocardiogram, the method comprising:
    a) receiving a plurality of real-time images representing a portion of the human body;
    b) identifying a feature of the portion of the human body within said plurality of images;
    c) calculating, as a function of the identified feature, a position on which to apply first, second, and third electrodes on the portion of the human body;
    d) displaying a real-time image representing said portion of the human body and further comprising a first positioning mark, a second positioning mark and a third positioning mark, wherein the first, second, and third positioning marks represent positions on which to apply, respectively, the first, the second and the third electrode.

11. A method for controlling the acquisition of an electrocardiogram according to claim 10,
    wherein step a) comprises receiving the plurality of real-time images representing shoulders, a chest, an abdomen and a pelvis of the human body,
    wherein step b) comprises identifying the position of the shoulders within at least part of said plurality of images,
    wherein step c) comprises:
        c1) calculating the width of the shoulders as a function of at least part of said plurality of images;
        c2) calculating, as a function of the width of the shoulders and a value of a first parameter, a first distance between the first positioning area and an extremity of the right shoulder and between the second positioning area and an extremity of the left shoulder;
        c3) calculating the width of the pelvis;
        c4) calculating, as a function of the width of the pelvis and of the value of a second parameter, a second distance between the third positioning area and an extremity of the left pelvis;
        c5) calculating a third distance between the third positioning area and the first positioning area equal to a value comprised in a range centered on half the width of the shoulders;
    wherein step d) comprises displaying the real-time image representing at least the chest of the human body,
    wherein:
        the first positioning mark includes a first positioning area in which to apply the first electrode, wherein the first electrode is positioned on the chest in proximity to the left shoulder and has a position identified by the first distance;
        the second positioning mark includes a second positioning area in which to apply the second electrode, wherein the second electrode is positioned on the chest in proximity to the right shoulder and has a position identified by the first distance;

the third positioning mark includes a third positioning area in which to apply the third electrode, wherein the third electrode is positioned on the abdomen in proximity to the leg left and has a position identified by the third distance and by the fourth distance.

12. A computer readable medium having a program comprising software code portions adapted to perform the method according to claim 10, when said program is executed on at least one computer.

\* \* \* \* \*